(12) United States Patent
Sera

(10) Patent No.: US 9,777,040 B2
(45) Date of Patent: Oct. 3, 2017

(54) GEMINI VIRUS REPLICATION INHIBITOR

(76) Inventor: Takashi Sera, Okayama (JP)

( * ) Notice: Subject to any disclaimer, the term of this patent is extended or adjusted under 35 U.S.C. 154(b) by 1165 days.

(21) Appl. No.: 13/702,473

(22) PCT Filed: Jun. 6, 2011

(86) PCT No.: PCT/JP2011/062891
§ 371 (c)(1),
(2), (4) Date: Feb. 20, 2013

(87) PCT Pub. No.: WO2011/155426
PCT Pub. Date: Dec. 15, 2011

(65) Prior Publication Data
US 2013/0160159 A1 Jun. 20, 2013

(30) Foreign Application Priority Data
Jun. 7, 2010 (JP) .................. 2010-129682

(51) Int. Cl.
*C12N 15/82* (2006.01)
*C07K 14/00* (2006.01)
*A01N 59/16* (2006.01)
*C07K 14/47* (2006.01)

(52) U.S. Cl.
CPC ............ *C07K 14/001* (2013.01); *A01N 59/16* (2013.01); *C07K 14/4702* (2013.01); *C12N 15/8283* (2013.01)

(58) Field of Classification Search
None
See application file for complete search history.

(56) References Cited

U.S. PATENT DOCUMENTS

2003/0082561 A1* 5/2003 Sera .................. C07K 14/4702
435/6.12

FOREIGN PATENT DOCUMENTS

| JP | 2004-519211 A | 7/2004 |
| WO | WO 02/08286 A2 | 1/2002 |
| WO | WO 2004/101798 A1 | 11/2004 |

OTHER PUBLICATIONS

Koshino-Kimura et al, Nucleic Acids Symposium Series (2009), 53: 281-282.*
Australian Office Action dated Mar. 13, 2014, issued in corresponding Australian Patent Application No. 2011262991.
Chinese Office Action and Search Report, dated Sep. 5, 2014, for Chinese Application No. 201180030222.2, with an English translation.
Eurasian Office Action, dated Sep. 10, 2014, for Eurasian Application No. 201291371/28, with an English translation.
Chinese Office Action dated Apr. 3, 2015, issued in corresponding Chinese Patent Application No. 201180030222.2.
Eurasian Office Action dated Jun. 2, 2015, issued in corresponding Eurasian Patent Application No. 201291371/28.
Japanese Office Action dated Jul. 7, 2015, issued in corresponding Japanese Patent Application No. 2012-519364.
Chinese Office Action dated Oct. 21, 2013, issued in corresponding Chinese Patent Application No. 201180030222.2 (English translation is provided).
Form PCT/ISA/210 mailed Aug. 30, 2011 for International Application No. PCT/JP2011/062891.
Forms PCT/IB/326, PCT/IB/373 and PCT/ISA/237, mailed Dec. 20, 2012, for International Application No. PCT/JP2011/062891.
Forms PCT/IB/338, PCT/IB/373 and PCT/ISA/237, mailed Jan. 17, 2013, for International Application No. PCT/JP2011/062891.
Kimura et al., "Jinko DNA Ketsugo Tanpakushitsu o Mochiita Tomato Oka Hamaki Virus no Fukusei Sogai," Japan Society for Bioscience, Biotechnology, and Agrochemistry 2009 nendo (Heisei 21 Nendo) Taikai Koen Yoshishu, 2009, p. 313, 3p118A (Only abstract provided).
Kimura et al., "Jinko DNA Ketsugo Tanpakushitsu o Mochiita Tomato Oka Hamaki Virus Taisei Shokubutsu no Kaihatsu," Heisei 22 nendo Phytopathological Society of Japan, Taikai Program Koen Yoshi Yokoshu, Mar. 30, 2010, p. 110 (Only abstract provided).
Kimura et al., "Jinko DNA Ketsugo Tanpakushitsu o Mochiita Tomato Oka Hamaki Virus Taisei Shokubutsu no Soshutsu," Japan Society for Bioscience, Biotechnology, and Agrochemistry 2010 nendo (Heisei 22 Nendo) Taikai Koen Yoshishu, Mar. 5, 2010, p. 118, 2AZp22 (Only abstract provided).
Koshino-Kimura et al., "Construction of plants resistant to TYLCV by using artificial zinc finger proteins," Nucleic Acids Symposium Series, No. 53, Sep. 27, 2009, pp. 281-282.
Koshino-Kimura et al., "Generation of plants resistant to tomato yellow leaf curl virus by using artificial zinc-finger proteins," Nucleic Acids Symposium Series, No. 52, pp. 189-190, Sep. 8, 2008, pp. 189-190.
Monci et al., "A natural recombinant between the geminiviruses Tomato yellow leaf curl Sardinia virus and Tomato yellow leaf curl virus exhibits a novel pathogenic phenotype and is becoming prevalent in Spanish populations," Virology, vol. 303, 2002, pp. 317-326.
Sera et al., "Rational Design of Artificial Zinc-Finger Proteins Using a Nondegenerate Recognition Code Table," Biochemistry, vol. 41. No. 22, Jun. 4, 2002, pp. 7074-7081.
Sera, "Inhibition of Virus DNA Replication by Artificial Zinc Finger Proteins," Journal of Virology, vol. 79, No. 4, Feb. 2005, pp. 2614-2619.
Takenaka et al., "Inhibition of tomato yellow leaf curl virus replication by artificial zinc-finger proteins," Nucleic Acids Symposium Series, No. 51, 2007, pp. 429-430.
Urbino et al., "A novel cloning strategy for isolating, genotyping and phenotyping genetic variants of geminiviruses," Virology Journal, vol. 5, No. 135, Oct. 31, 2008, 10 pages.
Chinese Office Action for corresponding Chinese Application No. 201180030222.2, dated Feb. 20, 2017, with an English translation thereof.
Office Action issued in corresponding Japanese Patent Application No. 2012-519364 on Nov. 22, 2016, with partial English language translation.
Japanese Office Action issued in Japanese Patent Application No. 2012-519364 on Oct. 6, 2015, with partial English translation.

* cited by examiner

*Primary Examiner* — Elizabeth McElwain
(74) *Attorney, Agent, or Firm* — Birch, Stewart, Kolasch & Birch, LLP

(57) ABSTRACT

A replication inhibitor, which is an agent for inhibiting replication of a geminivirus, and comprises a zinc finger protein that can specifically bind to at least full length of stem loop region DNA of the geminivirus, or a part thereof, and can inhibit formation of a stem loop structure.

19 Claims, 16 Drawing Sheets

Fig. 5

Tomato yellow leaf curl virus
  5'-GCGGCCATCCG   TATAATATTAC   CGGATGGCCGC-3'
Bean dwarf mosaic virus
  5'-GCGGCCATCCG   TATAATATTAC   CGGATGGCCGC-3'
Tomato golden mosaic virus
  5'-GCGGCCATCCG   TTTAATATTAC   CGGATGGCCGC-3'
Abutilon mosaic virus
  5'-GCGGCCATCCG   CTATAATATTAC  CGGATGGCCGC-3'
Bean golden mosaic virus
  5'-GCGGCCATCCG   CTATAATATTAC  CGGATGGCCGC-3
Potato yellow mosaic virus
  5'-GCGGCCATCCG   TTATAATATTAC  CGGATGGCCGC-3'
Tomato mottle virus
  5'-GCGGCCATCCG   CAATAATATTAC  CGGATGGCCGC-3'

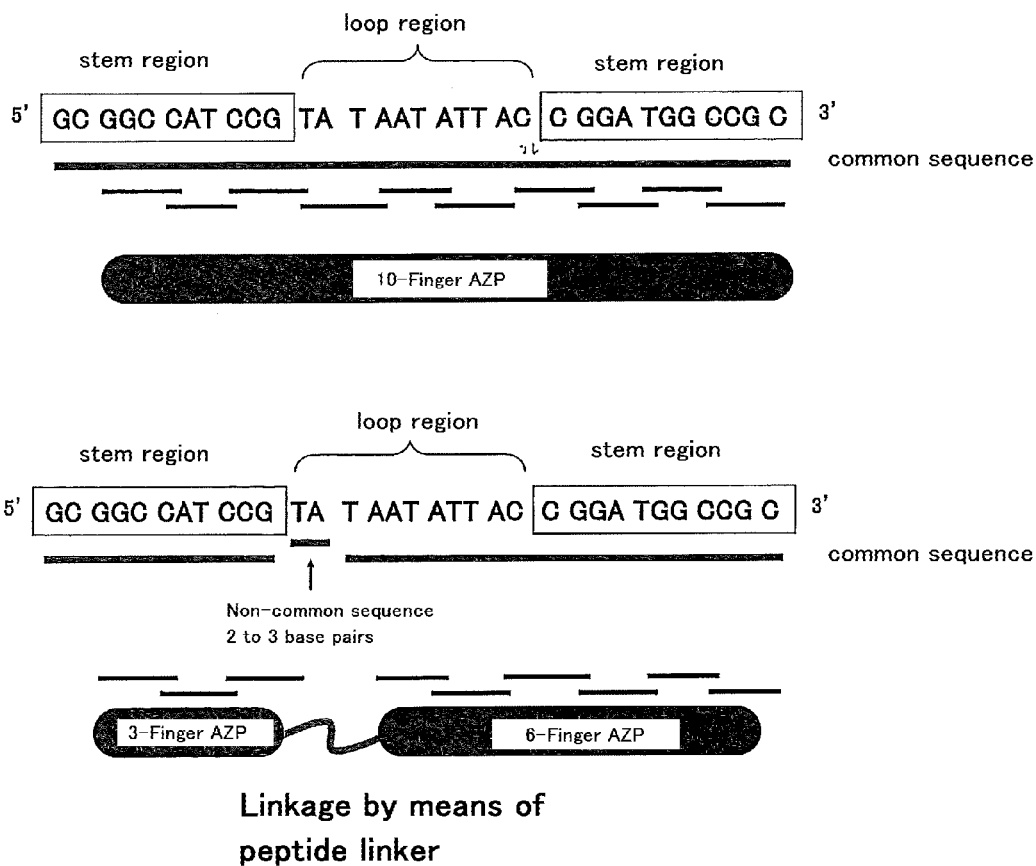

Fig. 6

Fig. 21
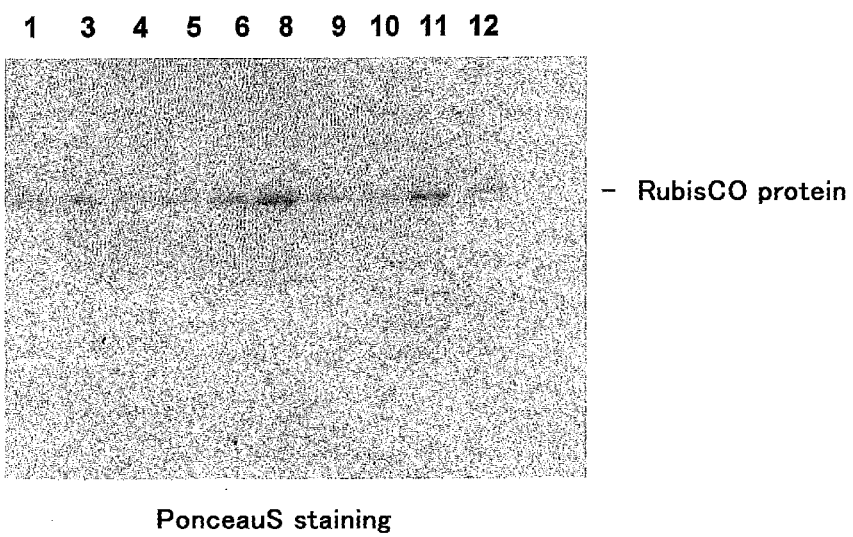
PonceauS staining
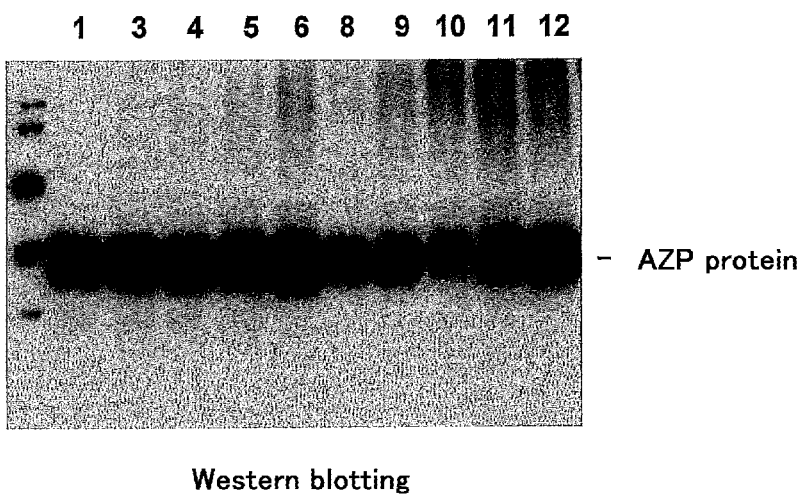
Western blotting

Fig. 22
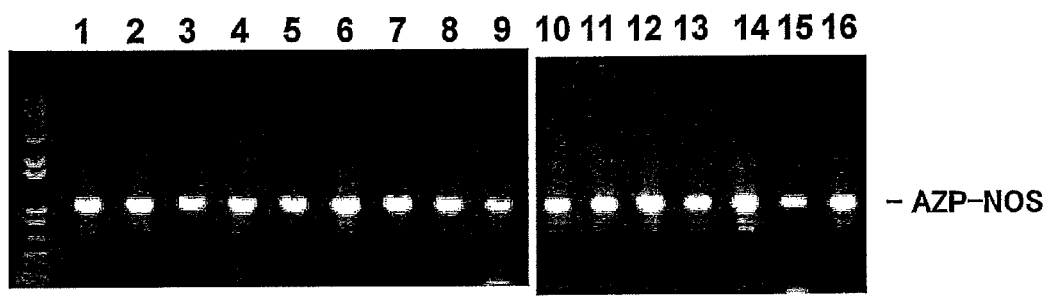
Fig. 23
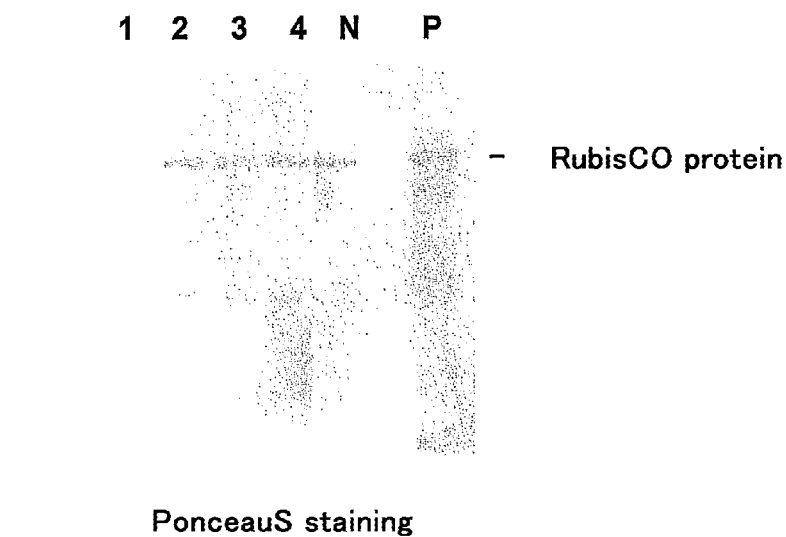
PonceauS staining
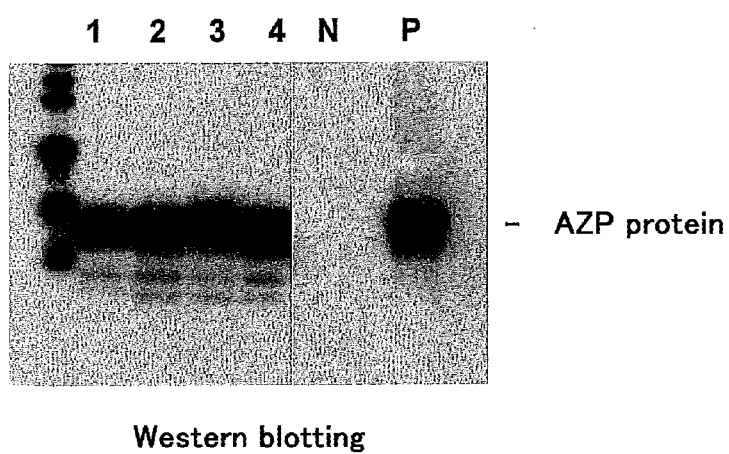
Western blotting Non-infected control    Infected indivisual plant Wild-type tomato AZP-2 transformed tomato

GEMINI VIRUS REPLICATION INHIBITOR

REFERENCE TO SEQUENCE LISTING SUBMITTED VIA EFS-WEB

This application includes an electronically submitted sequence listing in .txt format. The .txt file contains a sequence listing entitled "2016-04-18 2870-0556PUS1_ST25.txt" created on Apr. 18, 2016 and is 10,634 bytes in size. The sequence listing contained in this .txt file is part of the specification and is hereby incorporated by reference herein in its entirety.

TECHNICAL FIELD

The present invention relates to an effective means for controlling infection of plant viruses. More specifically, the present invention relates to a replication inhibitor against geminiviruses as plant viruses, a plant having resistance against geminivirus infection, and the like.

BACKGROUND ART

Zinc finger is one of DNA-binding motives, as well as the helix-turn-helix motif and the leucine zipper motif. It has two cysteine residues in the amino terminus region and two histidine residues in the carboxyl terminus region, and takes a three dimensional structure in which zinc (Zn) coordinates with these residues. Since zinc finger has an extremely strong DNA-binding ability, artificial DNA-binding proteins that utilize the motif to strongly bind to DNA (henceforth also referred to as "AZP" in this specification) have been proposed, and there have been reported AZPs designed so that they can recognize a specific nucleotide sequence by using the nondegenerate recognition code table (Japanese Patent Unexamined Publication (KOHYO) No. 2004-519211; Biochemistry, 41, pp. 7074-7081, 2002).

One zinc finger motif can recognize 3 or 4 bps and bind to the base pairs, and by connecting zinc fingers with a peptide linker, length of nucleotide sequence desired to be specifically bound by zinc fingers can be controlled. The fourth recognition nucleotide sequence of the zinc finger motif is an antisense strand, and overlaps with the first recognition nucleotide sequence of the following zinc finger motif, and therefore, N zinc finger motifs recognize a nucleotide sequence of 3N+1 bps, and bind thereto (see FIG. 1).

It has been reported that infection of plant DNA viruses can be controlled by using the AZP (J. Virology, 79, pp. 2614-2619, 2005). This publication reports infection-controlling effect of AZP for the plant DNA virus, beet severe curly top virus (BSCTV), in *Arabidopsis thaliana*. In this method, a means of inhibition by AZP is applied against the binding of a replication protein (Rep) to the Rep binding site (direct repeats) on the replication origin, which binding is required for the start of virus replication, and this method includes design of AZP to inhibit virus replication so that the AZP has a DNA-binding ability higher than that of Rep on the basis of the direct repeats of the replication origin. However, since the replication origin has a virus-specific nucleotide sequence, this method, including the block of the direct repeats of Rep by the AZP, has a problem that use of each different AZP is required against each of various plant viruses. From this point of view, it is desired to provide a means for achieving infection-controlling effect for various plant viruses with a single AZP.

Tomato yellow leaf curl is a viral disease of tomato plants and is induced by infection of the tomato yellow leaf curl virus (TYLCV). When the tomato yellow leaf curl is developed, green color of fresh leaves fades and yellows, leaves curl and then shrink, and the whole plant shows dwarfing, which results in arrest of growth. The tomato yellow leaf curl has caused serious damages in the Mediterranean sea coast, Africa, Middle and Near East, Asia, Central and South America, and the like. There are many isolated strains of TYLCV, and the TYLCV Israel strain (fulminant type, Nagasaki strain and Tosa strain), the TYLCV mild strain (mild type, Shizuoka strain and Aichi strain), and the like have so far been reported in Japan.

TYLCV belongs to the family Geminiviridae, and geminivirus is a generic name of viruses having one or two single-stranded cyclic DNAs that infect plants. Geminiviruses include various plant viruses, such as potato yellow mosaic virus and bean golden mosaic virus. If a means for inhibition can be provided against virus replication targeting a nucleotide sequence highly conserved in the geminiviruses, it is expected that TYLCV infection as well as infection with various plant viruses can be effectively controlled. Although the method disclosed in International Patent Publication WO2004/101798 and the like are known as a method for preparing a transformed plant having sustainable resistance against geminivirus, the approach thereof is completely different from that of the present invention.

PRIOR ART REFERENCES

Patent Documents

Patent document 1: Japanese Patent Unexamined Publication (KOHYO) No. 2004-519211
Patent document 2: International Patent Publication WO2004/101798

Non-Patent Documents

Non-patent document 1: Biochemistry, 41, pp. 7074-7081, 2002
Non-patent document 2: J. Virology, 79, pp. 2614-2619, 2005

SUMMARY OF THE INVENTION

Object to be Achieved by the Invention

An object of the present invention is to provide an effective means for controlling infection of a geminivirus. More specifically, the object of the present invention is to provide an agent for inhibiting replication of a geminivirus, a plant having resistance against a geminivirus, and the like.

Means for Achieving the Object

When a geminivirus enters into a plant, it first becomes a double-stranded cyclic DNA by utilizing an endogenous factor of the plant. Then, the replication protein (Rep) derived from the virus binds to the Rep-binding site locating upstream of a stem loop of intergenic region (IR). Rep is a multi-functional protein, and it binds to the Rep-binding site, introduces a nick into a nine-nucleotide sequence of the loop moiety of the stem loop, and covalently binds to the 5' end of the DNA introduced with the nick. Then, DNA synthesis is started from the 3' end by using one of the strands as the template, and when one copy of the genome is synthesized, a nick is introduced into the newly formed nine-nucleotide sequence by Rep. The DNA corresponding to one copy of the genome simultaneously excised is ligated by Rep, thus the single-stranded cyclic DNA is replicated, and Rep covalently binds to the newly formed 5' end. Replication of geminivirus is attained by repetition of this process, and all the materials required for the replication other than Rep are derived from the plant (refer to FIG. 2 as well as Kagaku to Seibutsu (Bioscience & Biotechnology), 41, pp. 311-317, 2003, and the like).

It is known that Rep cleaves only a single-stranded DNA, and in order for Rep to cleave a viral DNA, it is necessary that the viral DNA forms a stem loop structure. It is known that a nucleotide sequence that forms such stem loop is very highly conserved in geminiviruses. In general, the stem region consists of nine GC pairs and two AT pairs, and the loop region consists of 11 or 12 nucleotides, and comprises TT, TTT, TA, or ATA, followed by a nucleotide sequence of TAATATTAC (refer to Kagaku to Seibutsu, 41, pp. 311-317, 2003, p. 313, FIG. 2, and the like).

In order to provide a means that can commonly inhibit replication of various viruses belonging to the geminiviruses, the inventor of the present invention conducted various researches focusing on the stem loop moiety. As a result, the inventor found that when AZP was specifically bound to DNA of the stem loop moiety to stabilize the double-stranded structure of the viral DNA and thereby inhibit structural change thereof into the stem loop, cleavage of the viral DNA by Rep, which can cleave only a single-stranded DNA, was successfully inhibited. The inventor also found that this virus replication inhibitory action successfully functioned in a plant body. The present invention was accomplished on the basis of these findings.

The present invention thus provides a replication inhibitor for a geminivirus, which comprises a zinc finger protein that can specifically bind to full length DNA of stem loop region of the geminivirus, or one or more partial DNAs selected from the full length DNA, and can inhibit formation of a stem loop structure.

According to preferred embodiments of this invention, there are provided the aforementioned replication inhibitor, which contains a single zinc finger protein that can bind to one partial DNA selected from the full length DNA of the stem region of the geminivirus; the aforementioned replication inhibitor, which contains a single zinc finger protein that can bind to two or more partial DNAs selected from the full length DNA of the stem region of the geminivirus; the aforementioned replication inhibitor, wherein the zinc finger protein is a zinc finger protein containing ten zinc finger domains; the aforementioned replication inhibitor, which contains a zinc finger protein formed by binding two or more zinc finger proteins, with a linker or linkers, that are capable of binding to respective two or more partial DNAs selected from the full length DNA of the stem region of the geminivirus; the aforementioned replication inhibitor, which contains two zinc finger proteins; and the aforementioned replication inhibitor, wherein said two zinc finger proteins consist of a zinc finger protein comprising three zinc finger domains and a zinc finger protein comprising six zinc finger domains.

The present invention also provides a nucleic acid encoding the aforementioned zinc finger protein, and a replication inhibitor for a geminivirus, which contains a nucleic acid encoding the aforementioned zinc finger protein.

According to preferred embodiments of the aforementioned invention, there are provided the aforementioned replication inhibitor, wherein the geminivirus is a virus belonging to the genus *Begomovirus*; and the aforementioned replication inhibitor, wherein the geminivirus is a tomato yellow leaf curl virus.

As other aspects of the present invention, there are provided an anti-geminivirus agent, which comprises the aforementioned zinc finger protein or a nucleic acid encoding the aforementioned zinc finger protein; an infection-preventing agent for a geminivirus, which comprises the aforementioned zinc finger protein or a nucleic acid encoding the aforementioned zinc finger protein; and an agricultural chemical for controlling geminivirus infection, which comprises the aforementioned zinc finger protein or a nucleic acid encoding the aforementioned zinc finger protein.

As further aspects of the present invention, there are provided a method for preventing geminivirus infection of a plant, which comprises the step of applying a prophylactically effective amount of the aforementioned zinc finger protein or a nucleic acid encoding the aforementioned zinc finger protein to the plant; and a method for controlling geminivirus infection, which comprises the step of applying an amount effective for the control of the aforementioned zinc finger protein or a nucleic acid encoding the aforementioned zinc finger protein to a plant.

The present invention also provides a gene recombinant plant, which is a plant having resistance against a geminivirus, and can express the aforementioned zinc finger protein; a transformed plant, which is a plant having resistance against a geminivirus, and is introduced with a gene encoding the aforementioned zinc finger protein; and a method for allowing a plant to acquire resistance against a geminivirus, which comprises the step of transforming the plant with a gene encoding the aforementioned zinc finger protein.

The present invention further provides a recombinant vector, which contains a nucleic acid encoding the aforementioned zinc finger protein, and the aforementioned recombinant vector, which is used for transforming a plant so as to have resistance against a geminivirus. As the vector, a virus vector for plants and the like can be used.

Effect of the Invention

The replication inhibitor of the present invention targets the stem loop region highly conserved in geminiviruses, and therefore it can act as a replication inhibitor commonly usable against infection by various geminiviruses. Accordingly, the replication inhibitor of the present invention can exhibit high efficacy against not only infection by TYLCV, which is a typical virus of the geminiviruses, but also infection by other geminiviruses, and therefore it is extremely useful as a means for controlling various geminiviruses.

BRIEF DESCRIPTION OF THE DRAWINGS

FIG. 5 This figure depicts homology of the stem loop regions of several kinds of viruses encompassed by the geminiviruses (SEQ ID NOS: 13-19).

FIG. 6 This figure depicts an example of replication inhibitor targeting only TYLCV (upper part) (SEQ ID NO: 13) and an example of replication inhibitor targeting various geminiviruses (lower part) (SEQ ID NO: 20).

FIG. 21 This figure depicts the results of the confirmation of expression of AZP in T2 plants obtained by introducing AZP-2. AZP in the extracts of leaves of the T2 plants shown in FIG. 20 was detected by Western blotting using anti-HA antibodies. The lane numbers in this figure correspond to those of FIG. 20.

FIG. 22 This figure depicts the results of identification of homozygous T2 line for the inserted AZP gene performed by PCR for T3 plants obtained by introducing AZP-2. Results of PCR performed by using DNAs extracted from T3 plants derived from a specific transformant T2 (Lanes 1 to 16) are shown. This T2 plant, for which the inserted AZP gene was confirmed in all the T3 individuals, was selected as a homozygote.

FIG. 23 This figure depicts the results of confirmation of expression of AZP in T3 plants obtained by introducing AZP-2. Results of detection of AZP in extracts of leaves of T3 plants (Lanes 1 to 4), extract of leaves of a wild-type tomato (N), and extract of leaves of T2 plant of the line used (P) are shown, which detection was performed by Western blotting using anti-HA antibodies.

MODES FOR CARRYING OUT THE INVENTION

The replication inhibitor of the present invention is that for a geminivirus, and is characterized in that the inhibitor comprises a zinc finger protein that can specifically bind to full length DNA of the stem loop region of a geminivirus, or one or more partial DNAs selected from the full length DNA, and can inhibit formation of a stem loop structure.

Figure 1:
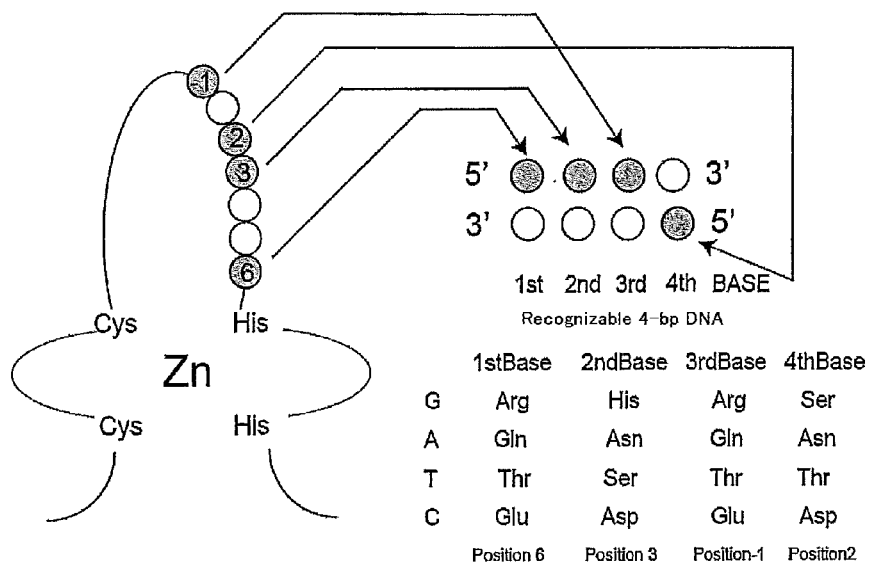
FIG. 1 This figure depicts the binding scheme of the zinc finger motif and DNA.
Figure 2:
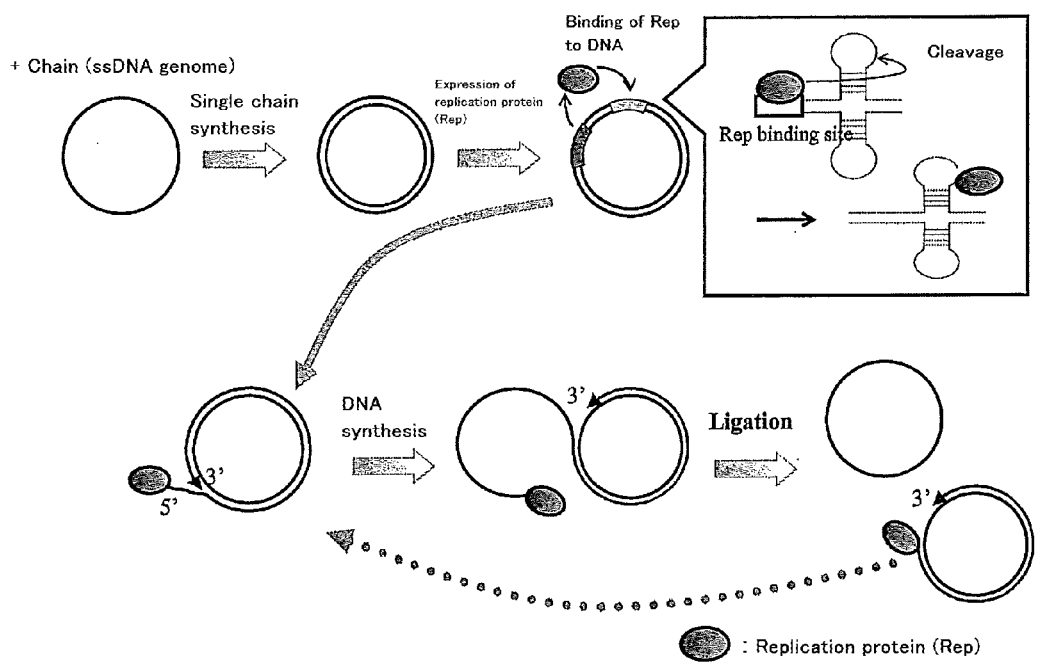
FIG. 2 This figure depicts a conceptual figure of the replication process of geminivirus.

The term "geminivirus" used in this specification means a DNA virus that infects plants, and has one or two single-stranded cyclic DNAs, and the means of this term is specifically explained in, for example, Kagaku to Seibutsu, 41, pp. 311-317, 2003, and the like. The geminiviruses are classified into the following four genera, namely, the genera *Mastrevirus, Curtovirus, Topocuvirus*, and *Begomovirus*, according to the genome structure, host spectrum, and type of vector insect. The replication inhibitor of the present invention can target arbitrary viruses belonging any of these genera. The genome structures of the viruses belonging to these genera are specifically shown in FIG. 2 of the aforementioned publication (Kagaku to Seibutsu, 41, pp. 311-317, 2003). Further, as for viruses belonging to the geminiviruses and abbreviations thereof, for example, detailed tables are mentioned in International Patent Publication WO2004/101798. The entire disclosure of International Patent Publication WO2004/101798 is incorporated into the disclosure of this specification by reference. It should be understood that the geminiviruses include known geminiviruses as well as unknown geminiviruses and new species as mutants of known geminiviruses.

Examples include, for example, viruses belonging to the genus *Mastrevirus* such as MSV (maize streak virus), WDV (wheat dwarf virus), and BeYDV (bean yellow dwarf virus), viruses belonging to the genus *Curtovirus* such as BCTV (beet curly top virus), viruses belonging to the genus *Topocuviruss* such as TPCTV (tomato pseudo-curly top virus), BGMV (bean golden mosaic virus), ACMV (African cassava mosaic virus), SLCV (squash leaf curl virus), TGMV (tomato golden mosaic virus), TYLCV (tomato yellow leaf curl virus), and the like, but the examples are not limited to these examples.

Figure 3:
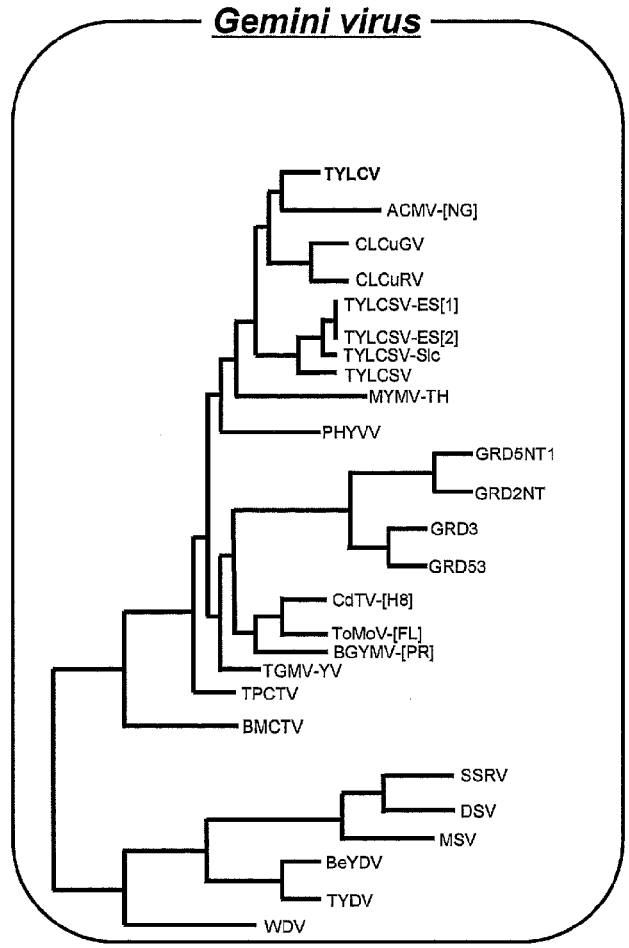
FIG. 3 This figure depicts the inclusive relationship of geminivirus and TYLCV.

The viruses belonging to the genus *Begomovirus* are preferred, from a viewpoint of homology of the stein loop region that serves as the binding site of the replication inhibitor. Preferred examples include TYLCCNV, TYLCGV, TYLCMaIV, TYLCSV, TYLCTHV, TYLCV, ACMV, BGMV, CaLCuV, ToCMoV, TGMV, ToGMoV, ToMHV, ToMoTV, ToMoV, ToRMV, ToSLCV, ToSRV, cotton leaf crumple or curl viruses (CLCrV, CLCuAV, ClCuGV, CLCuKV, CLCuMV, CLCuRV), East African cassava mosaic viruses (EACMCV, EACMMV, EACMV, EACMZV), potato yellow mosaic viruses (PYMPV, PYMTV, PYMV), squash leaf curl viruses (SLCCNV, SLCV, SLCYV), sweet potato leaf curl viruses (SPLCGV, SPLCV), tobacco leaf curl viruses (TbLCJV, TbLCKoV, TbLCYNV, TbLCZV), tomato leaf curl viruses (ToLCBV, ToLCBDV, ToLCGV, ToLCKV, ToLCLV, ToLCMV, ToLCNDV, ToLCSLV, ToLCTWV, ToLCVV, ToLCV), and the like, but preferred examples are not limited to these examples. In particular, TYLCV belonging to the genus *Begomovirus*, and the like are preferred objects for application of the replication inhibitor of the present invention. The inclusive relationship of the class of geminivirus and TYLCV is shown in FIG. 3.

Figure 4:
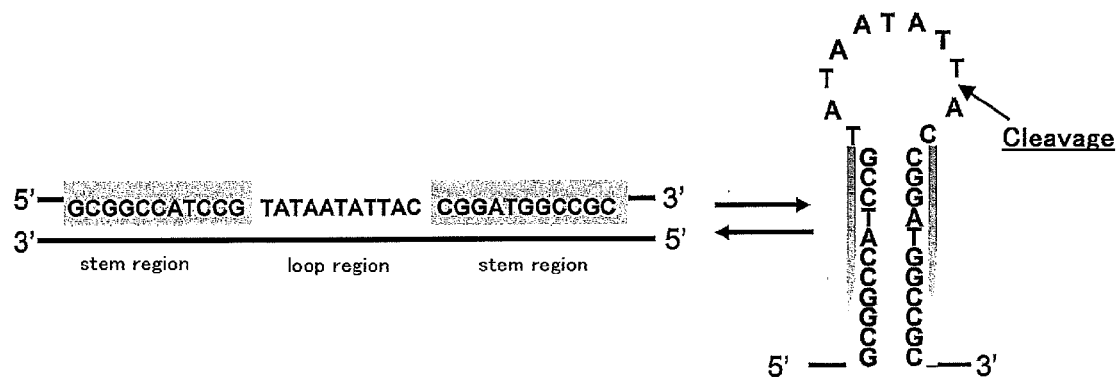
FIG. 4 This figure depicts the stem loop region of TYLCV (SEQ ID NO: 13).

The replication inhibitor of the present invention contains a zinc finger protein that can specifically bind to full length DNA of the stem loop region of a geminivirus, or one or more partial DNAs selected from the full length DNA, and has a function of inhibiting formation of the stem loop structure. The term "stem loop region" of geminivirus is explained below for the case of TYLCV as an example. The stem loop region is a region of 33 nucleotides consisting of two stem regions complementarily binding to each other (regions each consisting of 11 nucleotides), and a loop region forming a loop between the stem regions (region consisting of 11 nucleotides). Although various strains are known for TYLCV, the nucleotide sequence of the stem loop region is well conserved in all the TYLCV strains. The stem loop region of TYLCV is shown in FIG. 4. The expression that the nucleotide sequence of the stem loop region is "well conserved" used in this specification means that nucleotide sequences to be compared have a homology of 80% or more, preferably 90% or more, more preferably 95% or more, still more preferably 97% or more, most preferably 99% or more.

This stem loop region is highly conserved also in other viruses belonging to the genus *Begomovirus*. For example, the stem loop region consisting of 34 nucleotides exists on CRs (common regions) of both DNAs of BGMV, and the nucleotide sequences thereof have an extremely high homology to nucleotide sequences of the stem loop regions of other viruses belonging to the genus *Begomovirus*. Further, the stem loop region is also highly conserved in viruses belonging to the other genera of geminivirus. Homology of the stem loop regions of several kinds of viruses encompassed by the geminiviruses is shown in FIG. 5.

The replication inhibitor of the present invention can be designed so that it specifically binds to full length DNA of the stem loop region of the geminivirus, which is highly conserved as described above, or binds to one partial DNA or two or more partial DNAs selected from the full length DNA, and can inhibit formation of the stem loop structure, as a result of the specific binding. The replication inhibitor of the present invention can also be designed so that, in addition to the property of specifically binding to the full length DNA of the stem loop region, or to one or more partial DNAs selected from the full length DNA, it specifically binds to a DNA locating upstream and/or downstream of the stem loop region DNA. In order to inhibit the formation of the stem loop structure by specific binding, it is sufficient that the double strand structure of the viral DNA is stabilized by binding of the inhibitor of the present invention to the stem loop region, and a zinc finger protein that inhibits the formation of the stem loop structure can be designed by choosing an appropriate zinc finger domain on the basis of the nucleotide sequence of the stem loop region.

The zinc finger domain contained in the zinc finger protein can be designed so that it can recognize a specific nucleotide sequence by using the nondegenerate recognition code table. In this specification, the zinc finger domain means a domain constituting the DNA-binding site existing in the zinc finger protein, and it may be also simply called "finger". A zinc finger protein typically contains about two, three, four, six, or ten of zinc finger domains. The nondegenerate recognition code table and a method for designing a zinc finger protein that recognizes a specific nucleotide sequence and specifically binds thereto are described in, for example, Japanese Patent Unexamined Publication (KOHYO) No. 2004-519211. The entire disclosure of the above patent publication is incorporated in the disclosure of the present specification by reference. Further, Biochemistry, 41, pp. 7074-7081, 2002, and the like can also be referred to. As described above, information on the nucleotide sequence of the stem loop region of geminivirus genomic DNA can be easily obtained, and those skilled in the art can easily design and prepare a zinc finger protein that can specifically bind to at least the full length DNA of the stem loop region, or one partial DNA or two or more partial DNAs selected from the full length DNA.

For example, in order to design a replication inhibitor targeting only TYLCV, zinc finger proteins that can bind to a DNA containing the full length or substantially full length of the stem loop region DNA (33 nucleotides) well conserved in TYLCVs can be designed, and by using one kind of zinc finger protein selected from such zinc finger proteins as the replication inhibitor of the present invention, it becomes possible to inhibit replication of all types of TYLCV. As such zinc finger protein, for example, a zinc finger protein containing ten zinc finger domains can be designed. It is easily understood by those skilled in the art that the aforementioned technique can be suitably applied to the design of the replication inhibitor targeting viruses of the geminivirus family other than TYLCV.

Further, in order to design the replication inhibitor targeting various geminiviruses in addition to TYLCV, a single zinc finger protein that binds to two or more partial DNAs selected from the full length DNA of the stem region as sequences commonly contained in the targeted geminiviruses can be designed, or two or more zinc finger proteins that binds to respective partial DNAs as mentioned above can be designed, and bound to each other with an appropriate linker(s) such as peptide linker(s). As the linker, a peptide linker comprising about 1 to 40, preferably 1 to 20, more preferably 1 to 10, amino acid residues, as well as a synthetic linker consisting of an alkylene chain, a polyethylene glycol chain, or the like, a sugar chain, and the like may be used. When two or more partial DNAs are selected from the full length DNA of the stem region, they are preferably selected so that they do not contain a partial DNA that is a non-consensus sequence of the stem regions of various geminiviruses as the target, and it is generally desirable to select DNAs as consensus sequences locating upstream and downstream of such a non-consensus sequence as the partial DNAs.

An example of the replication inhibitor targeting only TYLCV, and an example of the replication inhibitor targeting various geminiviruses are shown in FIG. 6. In the figure, the example of the replication inhibitor targeting only TYLCV is shown on the upside, and the example of the replication inhibitor targeting various geminiviruses is shown on the downside.

Preferred examples of the replication inhibitor of the present invention include (a) the replication inhibitor having the amino acid sequence shown as SEQ ID NO: 1 in Sequence Listing as the replication inhibitor targeting only TYLCV, and the replication inhibitor having the amino acid sequence shown as SEQ ID NO: 2 as the replication inhibitor targeting various geminiviruses. Further, (b) a protein consisting of an amino acid sequence comprising the amino acid sequence of SEQ ID NO: 1 or 2, but including deletion, substitution and/or addition of one or several amino acid residues, preferably about 1 to 5 amino acid residues, and having substantially the same replication inhibitory action as that of a protein comprising the amino acid sequence specified as SEQ ID NO: 1 or 2 can also be used as the replication inhibitor of the present invention, which falls within the scope of the present invention. Furthermore, (c) a protein having a homology of 70% or more, preferably 80% or more, more preferably 90% or more, to the amino acid sequence specified as SEQ ID NO: 1 or 2, and having substantially the same replication inhibitory action as that of a protein comprising the amino acid sequence specified as SEQ ID NO: 1 or 2 can also be used as the replication inhibitor of the present invention, which falls within the scope of the present invention.

As the nucleic acid used for preparing the replication inhibitor of the present invention, a nucleic acid comprising a DNA encoding the aforementioned protein (a) (DNA specified by the nucleotide sequence of SEQ ID NO: 3 or 4 in Sequence Listing), as well as a DNA encoding the protein (b) or (c) mentioned above can be used. The DNA encoding the protein (b) or (c) mentioned above includes, for example, a DNA capable of hybridizing with a DNA specified by the nucleotide sequence shown as SEQ ID NO: 3 or 4 under stringent conditions, and the like. Examples of such a DNA as mentioned above include a DNA that can be identified by performing hybridization using DNA as a probe and a filter on which DNA or DNA fragment derived from a colony or plaque is fixed at 65° C. in the presence of about 0.7 to 1.0 M NaCl according to the colony hybridization method, the plaque hybridization method, or the Southern blotting hybridization method, and then washing the filter with 0.1 to 2×SSC solution (1×SSC solution contains 150 mM sodium chloride and 15 mM sodium citrate) at 65° C. For example, a DNA having a homology of 70% or more, preferably 80% or more, more preferably 90% or more, further more preferably 95% or more, most preferably 98% or more, to the nucleotide sequence of DNA used as the probe can be preferably used.

The replication inhibitor of the present invention is provided in the form of the aforementioned zinc finger protein or a nucleic acid encoding the zinc finger protein, and by applying the replication inhibitor of the present invention per se to a plant as an agricultural chemical, infection of a geminivirus can be controlled. Although the application method of the replication inhibitor of the present invention is not particularly limited, the inhibitor can be prepared, for example, as a composition for agricultural chemicals by using formulation additives well known in this field. Compositions for agricultural chemicals containing a protein or a nucleic acid as an active ingredient are known in this industry, and a composition for agricultural chemicals can be prepared by using an appropriate means. Examples of the means include, for example, a method of introducing the aforementioned nucleic acid into a plant cell by using a vector such as plasmid incorporated with the aforementioned nucleic acid to transiently transform the plant, a method of incorporating the aforementioned nucleic acid into a plant genome by using a vector, and the like, but the examples are not limited to these methods. Vectors usable for the method of the present invention include virus vectors that can infect plants.

The form of the composition for agricultural chemicals is not particularly limited, and any form usable in this industry can be employed. For example, there can be used compositions in the form of, for example, emulsion, solution, oil, water-soluble preparation, wettable powder, flowable formulation, powder, fine granule, granule, aerosol, fumigant, paste, or the like. The method for producing the composition for agricultural chemicals is also not particularly limited, and methods available for those skilled in the art can be appropriately employed. Further, active ingredients of other agricultural chemicals such as other antiviral agents, pesticides, fungicides, insecticide-fungicide combinations, and herbicides can also be blended in the composition for agricultural chemicals.

The present invention provides a transformed plant that can express the aforementioned replication inhibitor. In the present invention, the plant as an object of the transformation is not particularly limited, and it may consist of any of the whole plant body, plant organ (for example, leaf, petal, stem, root, seed, and the like), plant tissue (for example, epidermis, phloem, parenchyma, xylem, vascular bundle, palisade tissue, spongy parenchyma, and the like), and cultured plant cell. Type of the plant is not also particularly limited, and an arbitrary plant can be used as the object. It is preferable to choose a plant species in which infection of a geminivirus can be established as the object.

More specifically, examples of the plant species include, for example, plants belonging to the families Malvaceae (okra, and the like), Chenopodiaceae (beet, spinach, and the like), Brassicaceae (turnip, cauliflower, broccoli, cabbage, *Brassica campestris*, stock, radish, bok choy, Chinese cabbage, wasabi, and the like), Iridaceae (iris, gladiolus, freesia, and the like), Plumbaginaceae (statice, and the like), Poaceae (rice plant, lawn grass, corn, wheat, and the like), Gesneriaceae (saintpaulia, and the like), Araliaceae (*Aralia*

*cordata*, and the like), Cucurbitaceae (pumpkin, cucumber, *Cucumis melo* var. *conomon*, watermelon, melon, and the like), Ebenaceae (persimmon, and the like), Compositae (gerbera, *Chrysanthemum morifolium*, common marigold, cosmos, burdock, *Senecio cruenta*, *Chrysanthemum coronarium*, dahlia, sunflower, *Petasites japonicus*, margaret, *Gymnaster savatiereri*, lettuce, and the like), Juglandaceae (walnut, and the like), Moraceae (fig, mulberry, hop, and the like), Papaveraceae (Iceland poppy, and the like), Scrophulariaceae (snapdragon, and the like), Primulaceae (cyclamen, primula, and the like), Araceae (*Amorphophallus rivieri, Colocasia antiquorum* var. *esculenta*, and the like), Cactaceae (cactus, and the like), Lamiaceae (salvia, labiate, and the like), Begoniaceae (begonia, and the like), Zingiberaceae (ginger, *Zingiber mioga*, and the like), Nymphaeaceae (lotus, and the like), Violaceae (pansy, and the like), Umbelliferae (*Oenanthe stolonifera*, celery, carrot, parsley, Japanese honewort, and the like), Chloranthaceae (*Sarcandra glabra*, and the like), Ericaceae (various berries, and the like), Theaceae (*Thea sinensis*, and the like), Euphorbiaceae (poinsettia, and the like), Solanaceae (potato, tobacco, tomato, aubergine, pimento, *Capsicum annuum* var. *angulosum*, and the like), Caryophyllaceae (carnation, *Gypsophila paniculata*, and the like), Rosaceae (prune, strawberry, plum, cherry, *Prunus salicina*, Japanese pear, rose, *Eriobotrya japonica*, peach, *Spiraea thunbergii*, apple, pear, and the like), Convolvulaceae (morning glory, sweet potato, and the like), Geraniaceae (geranium and the like), Vitaceae (grape, and the like), Fagaceae (*Castanea crenata*, and the like), Paeoniaceae (peony, *Paeonia albiflora*, and the like), Actinidiaceae (kiwi fruit, and the like), Leguminosae (azuki bean, *Phaseolus vulgaris*, kidney beans, green soybeans, *Pisum sativum*, sweet pea, broad bean, soybeans, peanut, and the like), Rutaceae (various citruses, and the like), Dioscoreaceae (Chinese yam, and the like), Saxifragaceae (cymbidium, and the like), Liliaceae (asparagus, onion, tulip, *Allium tuberosum*, garlic, Welsh onion, hyacinth, lily, shallot, scallion, and the like), Orchidaceae (cattleya, hydrangea, phalaenopsis, and the like), Agavaceae (dracaena, and the like), and Gentianaceae (*Eustoma russellianum, Gentiana scabra* var. *buergeri*, and the like), but the examples are not limited to these examples.

Preferred examples include, for example, tomato, pepper, tobacco, pumpkin, manioc, sweet potato, cotton, melon, potato, soybean, wine cup, corn, wheat, sugarcane, bean, beet, watermelon, okra, cassava, and the like, but not limited to these examples. More preferred plants are tomato, cotton, potato, and the like, and a particularly preferred plant is tomato.

Examples of the plant source to be transformed include protoplast, seed, sprout, seedling, callus, cultured cell, plant body, and the like, but it is not particularly limited. Depending on the type of the objective plant, those skilled in the art can choose an appropriate part and perform transformation.

Although type of the vector used for the transformation is not particularly limited, it is preferred that the vector contains a promoter and/or enhancer sequence for expressing a gene encoding the aforementioned zinc finger protein. Types of the promoter and enhancer sequences are not particularly limited, so long as the sequence is capable of expressing the aforementioned gene in a plant cell, and arbitrary promoter and enhancer sequences can be used. For example, there can be used promoters and the like derived from a plant body, plant virus, or a bacterium including those of the genes of *Agrobacterium* or *Rhizobium* bacteria expressed in a plant cell, and the like. As the promoter, there can be used, for example, a promoter derived from T-DNA of *Agrobacterium tumefaciens*, Sinas promoter, cinnamyl alcohol dehydrogenase promoter, NOS promoter, ribulose bisphosphate carboxylase oxygenase (Rubisco) promoter, GRP1.8 promoter, 35S promoter derived from cauliflower mosaic virus (CaMV), promoter and enhancer for actin, histone, and the like derived from a plant, and the like, but the promoter and enhancer are not limited to these examples.

The vector may contain any of sequences of various antibiotic resistance genes and other marker genes as a selection marker gene. Example of the marker gene include, for example, spectinomycin resistance gene, streptomycin resistance gene, kanamycin resistance gene, geneticin resistance gene, hygromycin resistance gene, resistance gene for herbicide that inhibits acetolactate synthetase (ALS), resistance gene for herbicide that inhibits glutamine synthetase (for example, bar gene), β-glucuronidase gene, luciferase gene, and the like, but the examples are not limited to these examples.

In order to enhance gene expression efficiency, for example, it may be preferable to add a poly(A)+ sequence to the 3' end of a polynucleotide coding region in a coding region of a gene. As the poly(A)+ sequence, those derived from various plant genes or those derived from T-DNA can be used, but the sequence is not limited to these examples. Another sequence useful for expressing a gene at a high level, for example, an intron sequence of a specific gene, a sequence of 5' non-translation region, or the like may be introduced into the vector. Further, in order to promote migration into the nucleus, it is also preferable to incorporate a nuclear localization signal (NLS), or the like.

Vectors useful for gene expression in higher plants are well known in this field, and an arbitrary vector among them can be used. For example, examples of vector that can incorporate a part of DNA of the vector into the genome of a host plant when the vector is introduced into a plant cell as the host include a vector derived from the Ti plasmid of *Agrobacterium tumefaciens* as well as KYLX6, pKYLX7, pBI101, pBH2113, pBI121, and the like derived from the Ti plasmid, but the examples are not limited to these examples.

The expression vector can be introduced into a desired plant cell by using a known method for introducing a foreign gene into a plant cell, for example, the particle gun method, electroporation method, polyethylene glycol (PEG) method, calcium phosphate method, DEAE dextran method, microinjection, lipofection method, microorganism-mediated transfection method such as the *Agrobacterium* method, and the like. Among these, the particle gun method, electroporation method, polyethylene glycol method, *Agrobacterium* method, and the like are preferred, and the *Agrobacterium* method can be most preferably used (Methods Mol. Biol, 82, pp. 259-266, 1998). By using a binary vector method, gene recombination may be efficiently performed.

The method for constructing an expression vector and the method for transforming a plant are explained in more detail in the example section of the present specification. Accordingly, those skilled in the art can transform a desired plant so that it expresses the replication inhibitor of the present invention by referring to the aforementioned general explanations and specific explanations in the example section, and appropriately modifying or altering type of the vector, sequence to be introduced into the vector, transformation method, and the like.

EXAMPLES

Hereafter, the present invention will be still more specifically explained with reference to examples. However, the scope of the present invention is not limited by the following examples.

Example 1

1. Materials and Methods (1) Design of AZP

Zinc finger proteins (zinc finger protein is henceforth referred to with an abbreviation "AZP" in the examples) that recognize the following respective two kinds of DNA regions were designed on the basis of the nondegenerate recognition code table described in Japanese Patent Unexamined Publication (KOHYO) No. 2004-519211.
a) The stem loop region conserved in TYLCV
b) The stem loop region conserved in geminiviruses In AZP shown in the upper part of FIG. 6 (only for TYLCV), ten zinc finger domains were contiguously bound. In AZP shown in the lower part of FIG. 6 (for various geminiviruses), two kinds of AZPs that recognize two regions conserved by geminiviruses in the stem loop region were bound with a short peptide.

(2) Preparation of AZP Expression Plasmids

Figure 7:
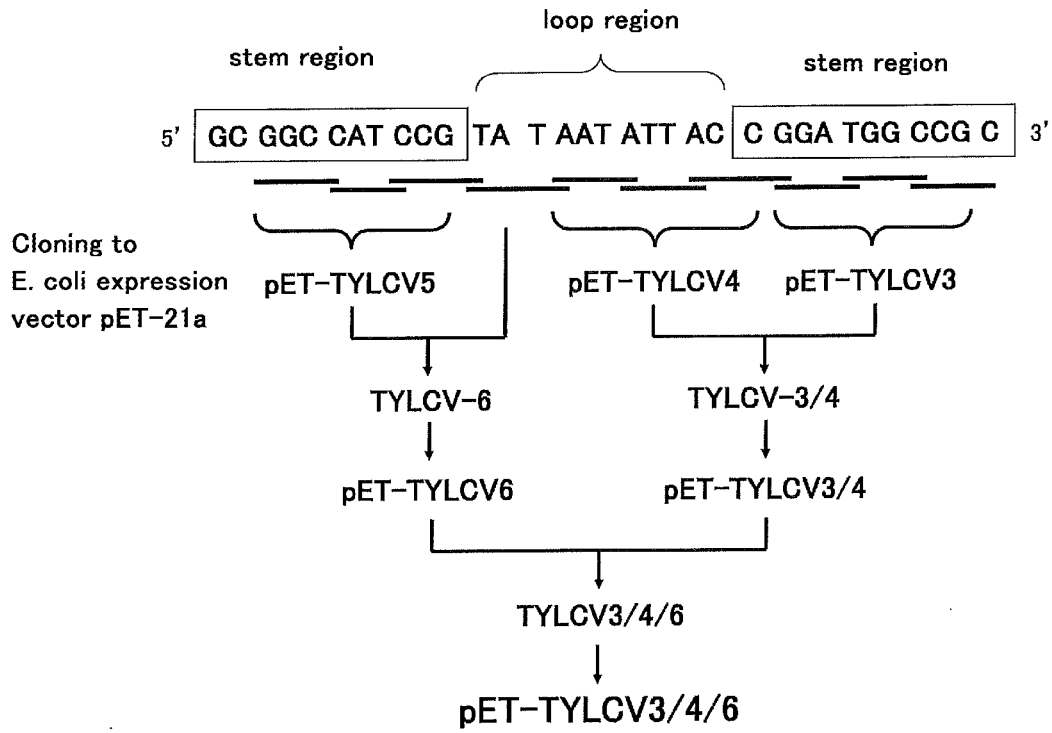
FIG. 7 This figure shows a scheme of preparation process of AZP-2 used only for TYLCV (SEQ ID NO: 13).

The AZP solely for TYLCV (henceforth referred to as "AZP-2") was prepared according to the scheme shown in FIG. 7. First, genes for three zinc fingers bound together were synthesized by PCR, and each cloned into the *Escherichia coli* expression vector pET-21a (Novagen) at the BamHI/HindIII sites, and the nucleotide sequences of the resulting plasmids were confirmed to obtain pET-TYLCV-3, pET-TYLCV-4, and pET-TYLCV-5. Then, the three-finger AZP genes in pET-TYLCV-3 and pET-TYLCV-4 were amplified by PCR and ligated to finally obtain pET-TYLCV3/4. A gene for zinc finger that recognizes 5'-TATA-3' was prepared, and ligated to the three-finger AZP gene in pET-TYLCV5 by the method mentioned above to prepare pET-TYLCV6. Finally, by amplifying the six-finger AZP gene and the four-finger AZP gene from pE-TYLCV3/4 and pET-TYLCV6 by PCR, respectively, and ligating them to prepare a plasmid (pET-TYLCV3/4/6) for expression of AZP-2 that recognizes 31 nucleotides among the 33 nucleotides forming the sequence of the stem loop region.

Figure 8:
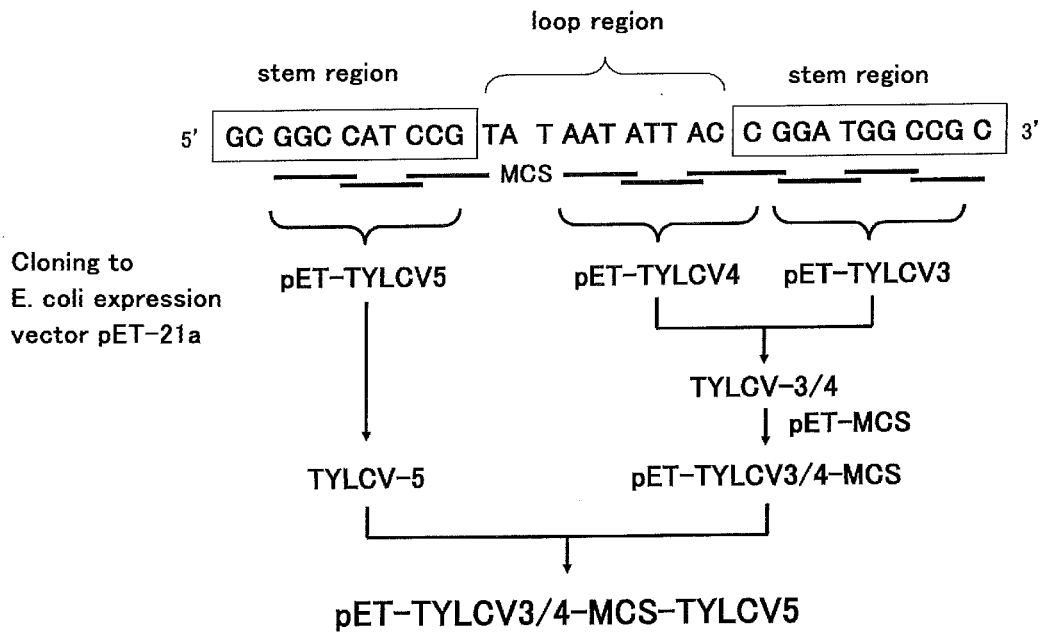
FIG. 8 This figure shows a scheme of preparation process of AZP-3 commonly usable for geminiviruses (SEQ ID NO: 20)

AZP generally applicable against geminiviruses (henceforth referred to as "AZP-3") was prepared according to the scheme shown in FIG. 8. First, in order to incorporate genes for two kinds of AZP that recognize two regions conserved by geminiviruses in the stem loop region and a linker peptide gene, a precursor plasmid (pET-MCS) was prepared. A gene for six-finger AZP that recognizes the longer region conserved in geminiviruses was amplified from pET-TYLCV3/4 by PCR, and cloned into pET-MCS to prepare pET-TYLCV3/4-MCS. Then, a gene for three-finger AZP that recognizes the shorter region conserved in geminiviruses was amplified from pET-TYLCV5 by PCR, and cloned into pET-TYLCV3/4-MCS to prepare a plasmid that expresses AZP-3 having 6 amino acid residues as a linker peptide (pET-TYLCV3/4-MCS-TYLCV5).

(3) Expression of AZP

*Escherichia coli* BL21(DE3) was transformed with each AZP expression plasmid, and the resulting transformant was cultured at 37° C. in the LB medium containing ampicillin. When $OD_{600}$ became 0.6 to 0.7, IPTG was added at a final concentration of 1 mM to induce expression of the objective protein. After culture for further 3 hours, *Escherichia coli* cells were collected by centrifugation, and stored at −80° C. until they were used for purification of proteins.

(4) Purification of AZP

Each AZP was purified by substantially the same method. The *Escherichia coli* cells stored at −80° C. were added with 10 ml of a lysis buffer (100 mM Tris-HCl, 100 mM NaCl, 0.1 mM $ZnCl_2$, 5 mM DTT, pH 8.0), and freezing and thawing were repeated 3 times to make the cell walls of *Escherichia coli* cells easily breakable. Then, the *Escherichia coli* cells were disrupted on an ultrasonicator, and centrifuged, and the supernatant containing the objective protein was collected. This supernatant was applied to a cation exchange resin Biorex-70 (Bio-Rad) to adsorb the objective protein to the resin, and the resin was sufficiently washed with a washing buffer (50 mM Tris-HCl, 50 mM NaCl, 0.1 mM $ZnCl_2$, 0.2 mM DTT, pH 8.0). Then, the objective protein was eluted with an elution buffer (50 mM Tris-HCl, 300 mM NaCl, 0.1 mM $ZnCl_2$, 0.2 mM DTT, pH 8.0). Only the fractions containing the objective protein were collected, concentrated by using an ultrafiltration membrane, and added with the same volume of glycerol, and then the mixture was stirred, and stored at −80° C. AZP purity was determined on the basis of amounts of bands stained in the Coomassie blue staining on SDS-PAGE gel. Concentrations of the proteins were determined by using Protein Assay ESL (Roche).

(5) Preparation of RepN Expression Plasmid

RepN is an N-terminus region of the virus replication protein Rep (191 amino acid residues), and has a DNA-binding ability. For use in an experiment for inhibition of binding of Rep to direct repeats by AZP, RepN was prepared by the following method. The RepN gene was amplified from the TYLCV genome by PCR using the TYLCV genome collected from an infected tomato plant, and cloned into pET-21a at the BamHI/HindIII sites in the same manner as that used for AZP. The nucleotide sequence of the resulting plasmid was confirmed to obtain a plasmid for expression of RepN (pET-RepN).

(6) Expression and Purification of RepN Protein

Expression of RepN was performed in the same manner as that used for expression of AZP, and sufficient expression amount was obtained. The resulting *Escherichia coli* cells were stored at −80° C. until they were used for purification of protein. RepN was purified in the same manner as that used for AZP. By ion exchange chromatography using Biorex-70, in which elution was performed with an elution buffer (50 mM Tris-HCl, 250 mM NaCl, 0.2 mM DTT, pH 8.0), RepN of high purity was successfully obtained.

(7) Evaluation of Abilities of AZP and RepN to Bind to Replication Origin

Target DNA sequence-binding ability of each protein was evaluated by the gel shift assay. A DNA oligomer containing the target DNA sequence was prepared, and labeled with $^{32}P$ at the 5' end. Then, a binding buffer (10 mM Tris-HCl, 100 mM NaCl, 5 mM $MgCl_2$, 0.1 mM $ZnCl_2$, 0.05% BSA, 10% glycerol, pH 7.5) containing the labeled DNA was added with a predetermined amount of the protein, and the reaction was continued for 1 hour on ice. This reaction product was applied to 6% non-denatured acrylamide gel, and electrophoresis was carried out at 4° C. for 2 hours (running buffer: 45 mM Tris-borate). After the electrophoresis, the gel was put on chromatography paper and dried. The paper was sufficiently dried, and then exposed to an X-ray film, and the band of the labeled DNA was detected. The protein concentration observed when the ratio of amounts of free DNA and DNA complex formed with the protein is 1:1 corresponds to the dissociation constant for the target DNA sequence. On the basis of that protein concentration, binding abilities of AZP and RepN were compared.

(8) Evaluation of Ability of AZP to Inhibit Cleavage by Virus Replication Protein (a) Preparation of Rep Expression Plasmid (1)

The full length of Rep having the cleavage activity was required for the evaluation of cleavage inhibition ability. Accordingly, a Rep expression plasmid was prepared. The Rep gene was amplified from the TYLCV genome by PCR in the same manner as that used for the preparation of the RepN expression plasmid, and cloned into pET-21a at the BamHI/HindIII sites. The nucleotide sequence of the resulting plasmid was confirmed to obtain a plasmid for expression of Rep (pET-Rep).

(b) Preparation of Rep Expression Plasmid (2)

Rep alone in the solubilized state after the disruption of the *Escherichia coli* cells may sometimes be not detected. Accordingly, Rep was prepared in the form of a fusion protein with glutathione S-transferase (GST), which promotes solubilization of hardly soluble proteins and can be easily purified. A DNA region containing the T7 promoter and the GST gene was amplified by PCR from a plasmid for expression of GST-fused protein (pET-41a, Novagen), and cloned into pET-Rep at the BamHI/SphI sites. The DNA sequence was confirmed to prepare a plasmid for expression of GST-Rep protein (pET-GST-Rep).

(c) Expression of GST-Rep Fusion Protein

Three kinds of *Escherichia coli*; BL21(DE3), Rosetta 2(DE3)pLysS, and BL21-Codon-Plus(DE3)-RIL, were each transformed with pET-GST-Rep, and expression was induced in each of the resulting clones with 1 mM IPTG at 37° C. in the same manner as that used for the expression of the RepN protein. Although the expression amount was the same for all the *Escherichia coli* strains, the largest solubilized amount of GST-Rep observed after disruption of the *Escherichia coli* cells was obtained with BL21(DE3). Therefore, the protein expression was performed by using the BL21(DE3) transformant at 30° C.

(d) Purification of GST-Rep Protein

The *Escherichia coli* pellet was suspended in 3 mL of a lysis buffer (4.3 mM $Na_2HPO_4$, 1.47 mM $KH_2PO_4$, 137 mM NaCl, 2.7 mM KCl, pH 7.3, 0.1 mM $ZnCl_2$, 5 mM DTT), and sonicated. After solubilization of the GST-Rep protein was confirmed by SDS-PAGE, centrifugation was performed, and only the supernatant was collected. A GST-binding resin washed with a 20-fold volume of 1×GST-bind wash buffer beforehand was transferred to a 15-mL conical flask, further washed with 5 mL of 1×GST-bind wash buffer (4.3 mM $Na_2HPO_4$, 1.47 mM $KH_2PO_4$, 137 mM NaCl, 2.7 mM KCl, pH 7.3), and centrifuged at 400×g and 25° C. for 5 minutes, and the supernatant was carefully removed. The supernatant containing the GST-Rep protein, obtained above after the sonication, was filtered through a 0.45-μm membrane filter, and added to the above pretreated resin. They were shaken overnight at 4° C. to adsorb the GST-AZP protein on the resin. This resin was put into a column, and washed with a washing buffer (4.3 mM $Na_2HPO_4$, 1.47 mM $KH_2PO_4$, 137 mM NaCl, 2.7 mM KCl, 0.1 mM $ZnCl_2$), and elution was performed with an elution buffer (50 mM Tris-HCl, pH 8.0, 0.1 mM $ZnCl_2$, 10 mM reduced glutathione). The eluted fractions were examined by SDS-PAGE, and the fractions containing GST-Rep protein were collected, and concentrated to a total volume of 300 μL by using an ultrafiltration membrane. Protein concentration was determined by using a commercial kit (Protein Assay ECL).

(e) Expression of GST-AZP Fusion Protein

An expression vector containing the GST-AZP gene for AZP-glutathione S-transferase (GST) fusion protein downstream from the T7 promoter was introduced into *Escherichia coli* cells. These *Escherichia coli* cells were cultured in the LB-Amp liquid medium (120 mL) until $OD_{600}$ became 0.65 to 0.75. After the culture, IPTG was added to a final concentration of 1 mM, and culture was further performed for 3 hours to induce expression of the GST-AZP protein. The *Escherichia coli* cells after the induction were collected by centrifugation, and stored at −80° C. The GST-AZP protein was purified in the same manner as that used for the purification of the GST-Rep protein.

(f) Evaluation of Ability of AZP to Inhibit Cleavage by Virus Replication Protein A reaction solution containing a labeled DNA (5 nM) consisting of 200 base pairs comprising the Rep-binding site (25 mM Tris-HCl, pH 7.5, 75 mM NaCl, 2.5 mM DTT) was added with GST-AZP (or GST-RepN for performance comparison experiment, or GST for control experiment), and they were mixed, and left standing on ice for 30 minutes. Then, the reaction mixture was added with GST-Rep and $MgCl_2$ at concentrations of 2 μM and 5 mM, respectively, and the reaction was continued at 25° C. After 30 minutes, the reaction was terminated by adding 2 μL of 0.5 M EDTA, and phenol treatment and ethanol precipitation were performed. A sample prepared by dissolution with 3 μL of a loading buffer (80% formamide, 10 mM EDTA) was electrophoresed on 8% denatured acrylamide gel.

2. Results (1) Evaluation of Ability of AZP to Bind to Target DNA Sequence

Figure 9:
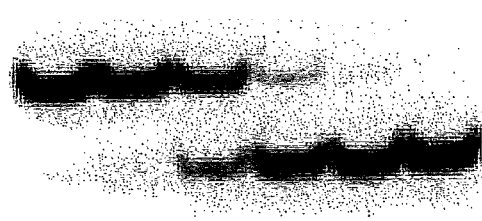
FIG. 9 This figure depicts results of evaluation of binding ability of AZP-2 by the gel shift assay to a target DNA sequence, which can be only used for TYLCV.
Figure 10:
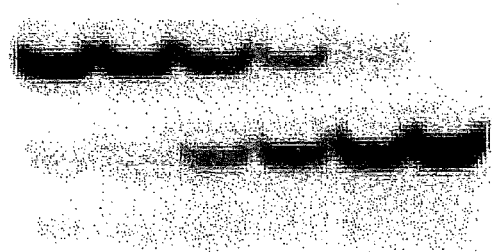
FIG. 10 This figure depicts results of evaluation of binding ability of AZP-3 by the gel shift assay to a target DNA sequence, which can be commonly used for geminiviruses.
Figure 11:
FIG. 11 This figure depicts results of evaluation of binding ability of RepN by the gel shift assay to a target DNA sequence for comparison.

Abilities of the purified AZP and RepN to bind to the target DNA sequence were evaluated by the gel shift assay. In this experiment, the DNA labeled with $^{32}P$ was added with the protein at various concentrations to perform the binding reaction, and then free DNA and DNA complex with the protein were separated on non-denatured gel. The protein concentration providing a ratio of bands of free DNA and DNA complex with the protein of 1:1 (corresponding to dissociation constant) was determined, and it was found that the dissociation constant of AZP-2 solely for TYLCV was 0.3 to 1 nM (FIG. 9), and the dissociation constant of AZP-3 generally applicable against geminiviruses was smaller than 10 nM (FIG. 10). Whilst, the dissociation constant of RepN was 30 nM (FIG. 11). From this experiment, it was revealed that the abilities of the designed AZP-2 and AZP-3 to bind to the target DNA sequence were both higher than that of Rep N.

Figure 12:
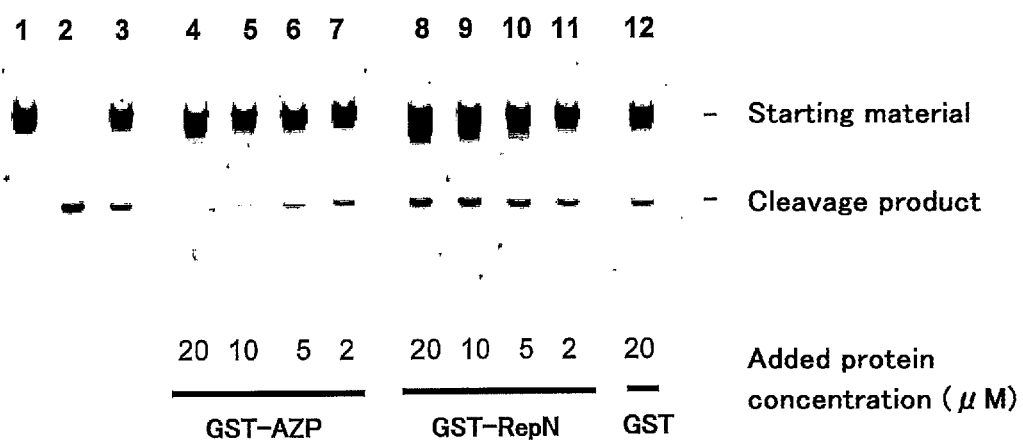
FIG. 12 This figure depicts inhibitory activity of GST-AZP (AZP-2) against cleavage of replication origin by Rep. The results for the substrate DNA (Lane 1), cleavage product marker (Lane 2), and cleavage product obtained with 2 μM GST-Rep (Lane 3) are shown.
Figure 13:
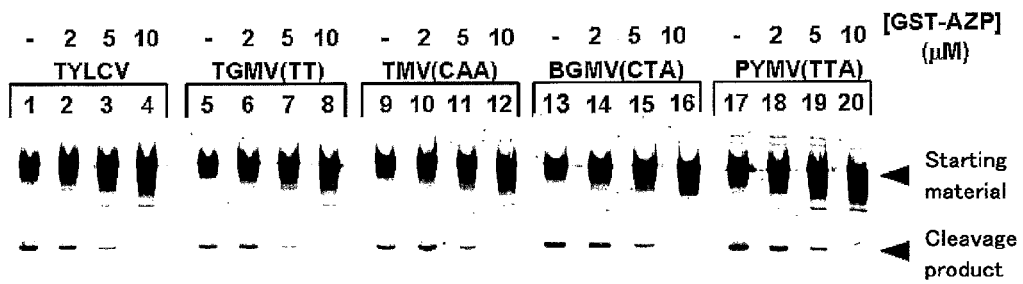
FIG. 13 This figure depicts inhibitory activity of GST-AZP (AZP-3) against cleavage of replication origin by Rep. Products of cleavage performed at a temperature of 25° C. for a reaction time of 30 minutes at a GST-Rep concentration of 2 μM are shown.

(2) Evaluation of Ability of AZP to Inhibit Cleavage by Virus Replication Protein As shown by the results of the lanes 4 to 7 shown in FIG. 12, the purified GST-AZP only for TYLCV (AZP-2) effectively inhibited cleavage by Rep at the replication origin. This inhibitory effect depended on the AZP concentration, and complete inhibition was observed at 20 μM. On the other hand, with RepN as a dominant negative form of Rep, no inhibition of the cleavage was observed (FIG. 12, lanes 8 to 11). RepN has a DNA-binding domain, and as readily understood, has completely the same DNA binding as that of Rep desired to be inhibited. No inhibition of the cleavage was observed with GST as shown by the result of the lane 12. Therefore, it was also revealed that the cleavage inhibitory activity of GST-AZP observed from the results of the lanes 4 to 7 entirely provided by AZP. Further, cleavage inhibitory ability of GST-AZP (AZP-3) was similarly evaluated. The results are shown in FIG. 13.

Example 2

Figure 14:
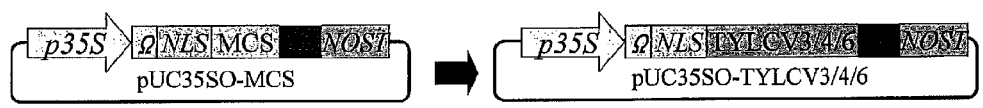
FIG. 14 This figure depicts preparation method of pUC35SO-TYLCV3/4/6: 35S: cauliflower mosaic virus-derived promoter, NLS: nuclear localization signal, Ω: 5' leader sequence for increasing translation efficiency, NOST: terminator, and TYLCV3/4/6: AZP that binds to consensus sequence in the entire TYLCV (recognition sequence is 5'-GGCCATCCGTATAATATTACCGGATGGCCGC-3') (SEQ ID NO: 21).
Figure 15:
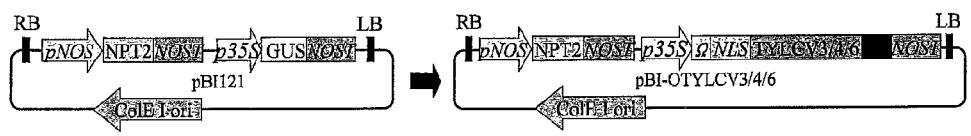
FIG. 15 This figure depicts preparation method of APZ expression plasmid for transformation: NOS: nopaline synthase promoter (derived from *Agrobacterium tumefaciens*), NPT2: kanamycin resistance gene, GUS: β-galactosidase gene, RB (right border) and LB (left border): repetition sequence of about 25 bps (DNA region between these sequences is transferred to the plant genome).
Figure 16:
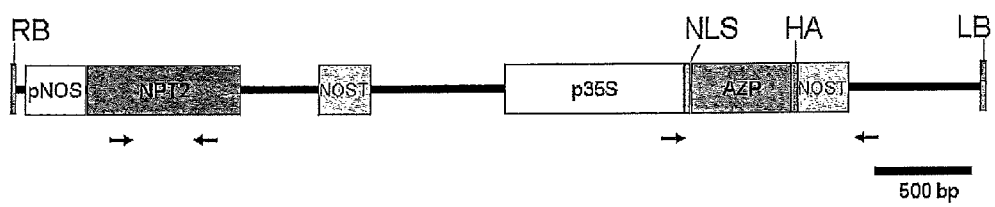
FIG. 16 This figure depicts a PCR primer set for detecting the structure of inserted gene, kanamycin resistance gene, and AZP gene in the transformant T1.
Figure 17:
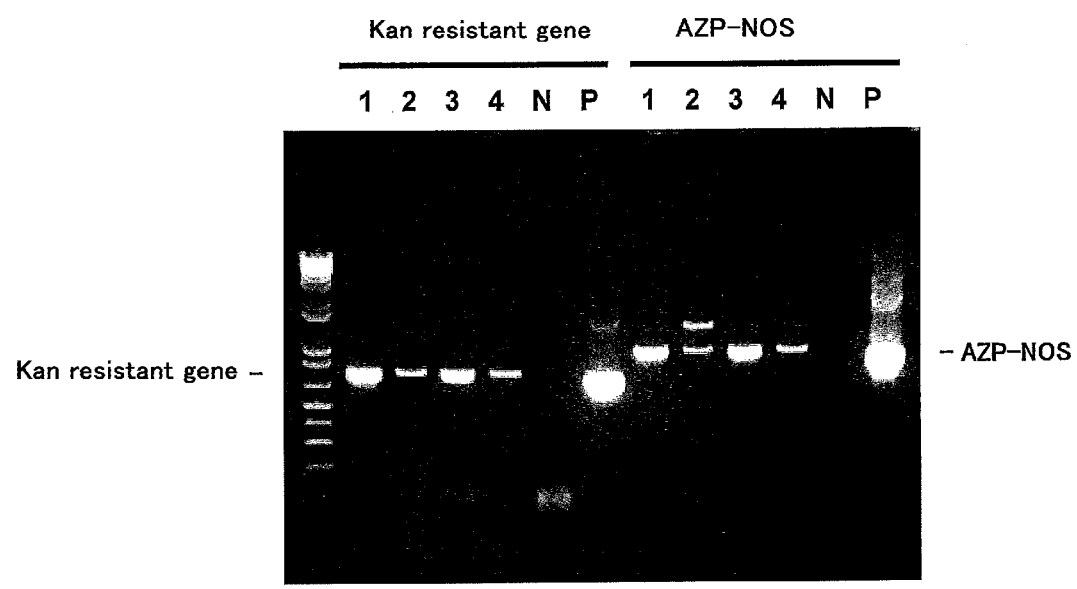
FIG. 17 This figure depicts the results of detection of the kanamycin resistance gene and the AZP gene in the transformant T1. The results of PCR performed by using DNA extracted from each T1 plant (Lanes 1 to 4), DNA extracted from a wild-type tomato (N), and the binary vector used for the transformation (P) are shown.
Figure 18:
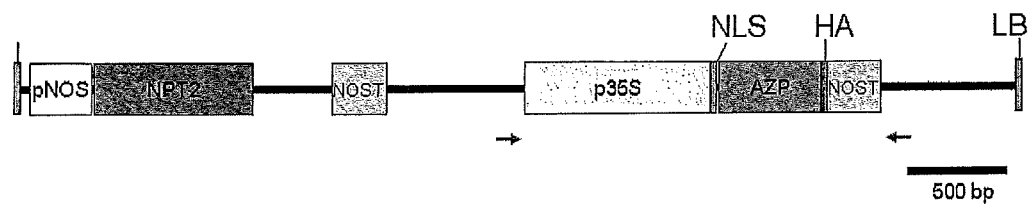
FIG. 18 This figure depicts a PCR primer set for confirming the structure of inserted gene in the whole region of the AZP expression cassette and insertion thereof into the genome.
Figure 19:
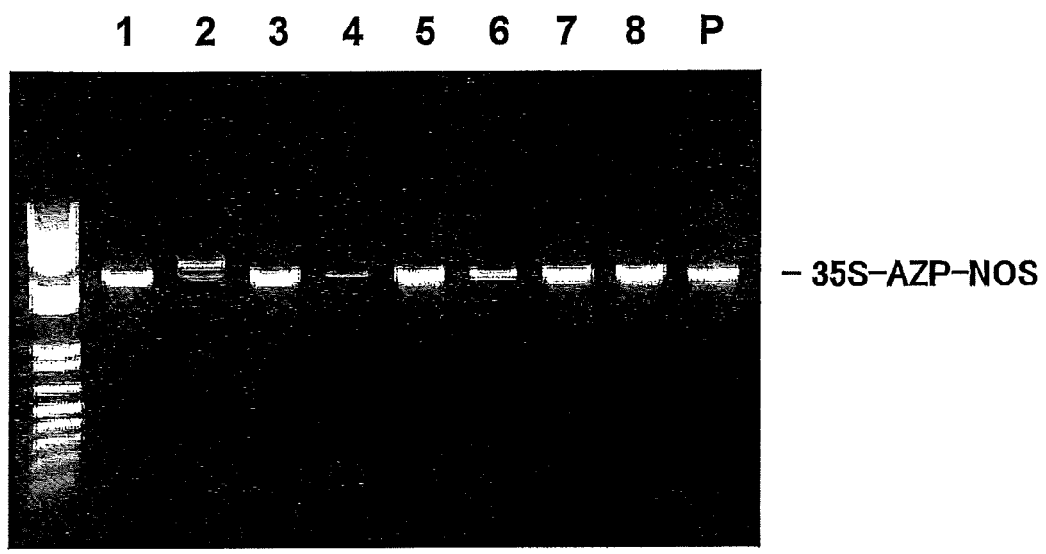
FIG. 19 This figure depicts the results of the confirmation of insertion of the AZP gene into the T2 plant obtained by introducing AZP-2, which confirmation was performed by PCR. The results of PCR performed for detection of the AZP expression cassette by using DNA extracted from each T1 plant (Lanes 1 to 8), and the binary vector used for the transformation (P) are shown.

1. Materials and Methods (1) Preparation of AZP-Transformed Tomato
(a) Preparation of Vector for Stable Expression of AZP in Plant Insertion of the gene encoding AFP-2 into a plant genome was attained by the *agrobacterium* method. For a protoplast experiment, pUC35SO-TYLCV3/4/6 was prepared from pUC35SO-MCS by the method shown in FIG. 14, and a region containing 35S promoter, AZP gene, and NOS terminator was excised from this plasmid with EcoRI and HindIII. The fragment was purified on agarose gel, and cloned into a binary plasmid pBI121 at the EcoRI/HindIII sites to obtain pBI-OTYLCV3/4/6. Correctness of the nucleotide sequence was confirmed by sequencing. The same procedure was also performed for AZP-3.

(b) Cultivation of Micro-Tom

Cultivation soil was filled in each well of a 72-well plastic tray, the soil was lightly wetted by using a watering pot, then one seed of Micro-Tom was sown on the soil of each well, the seed was covered with a small amount of wetted soil, and the whole tray was wrapped with Saran Wrap. The tray was placed in an artificial climate chamber (light period: 25° C. for 16 hours, dark period: 22° C. for 8 hours), and cultivation was performed. When germination was observed, Saran Wrap was removed, and the cultivation was continued under the same conditions. Two weeks after the seeding, each seedling was transferred to a plastic pot having a diameter of 12 cm, and cultivated until seeds were collected.

(c) Preparation of Seeds of Micro-Tom

Fruits of Micro-Tom ripened in red were collected, each divided into two on the equator line with a knife, and all the seeds were collected into a 50-ml plastic tube with a spatura. The seeds were gently washed with water, and then washed with 1% aqueous hydrochloric acid for 10 minutes to dissolve the gelatin layers around the seeds. Then, the seeds were washed with running water for 10 minutes, excessive moisture was absorbed with a paper towel, and the seeds were air-dried at room temperature for two days. The dried seeds were stored at 4° C.

(d) Gene Transfer into Micro-Tom Cotyledon

Ten to twenty seeds of Micro-Tom were sterilized with Haiter (Kao) diluted to 10%, and washed 4 times with sterilized water. These seeds were sown in a seeding medium (1×Murashige-Skoog (MS) medium, 15 g/L of sucrose, 3 g/L of Gelrite) compacted in a plant box, and growth was continued for 6 days under the conditions of 25° C. and 16-hour daylength. Individual plants of which true leaves grew to a size of about several millimeters were used for the transformation.

On the day before the *agrobacterium* infection, a glycerol stock (20 µL) of an *agrobacterium* C58C1RifR (GV2260) transformed with pBI-OTYLCV3/4/6 was inoculated to 2 mL of the LB medium (containing 100 mg/L of kanamycin and 50 mg/L of ampicillin), and culture was performed at 30° C. for 24 hours. On the day of the infection, the *agrobacterium* cell suspension (1 mL) was taken into an Eppendorf tube, and the cells were collected by centrifugation at 5,000 rpm for 5 minutes. These cells were suspended in 40 mL of the MS medium containing 100 µM acetosyringone and 10 µM mercaptoethanol.

A cotyledon of Micro-Tom was cut off with a razor, and cut into two around halfway from the tip end. These cotyledon sections were immersed into the aforementioned *agrobacterium* suspension, and left standing for 10 minutes to allow infection. The cotyledon sections were put on sterilized Kimtowel to absorb excessive suspension, and put into a co-culture medium (1×MS culture medium, 30 g/L of sucrose, 3 g/L of Gelrite, 1.5 mg/L of t-zeatin, 40 µM acetosyringone, 0.1% MES, pH 5.7). The lid of the culture vessel was sealed with a surgical tape, and culture was performed at 25° C. with shielding light with aluminum foil. After three to four days, the infected cotyledon sections were transferred to a callus induction medium (1×MS culture medium, 3 g/L of Gelrite, 1.5 mg/L of t-zeatin, 100 mg/L of kanamycin, 667 mg/L of Augmentin, 0.1% MES, pH 5.7). Calluses were formed from a part of the infected cotyledon sections in about two weeks, and some formed a shoot.

The calluses were subcultured in the fresh callus induction medium every two weeks. An individual plant that grew from the callus and formed 3 to 4 leaves, of which cotyledon section moiety was cut off, was transferred to a shoot induction medium (SIM medium, equivalent to CIM medium of which t-zeatin concentration is lowered to 1.0 mg/L) to promote growth of the shoot. When the shoot grew to a length of 1 to 2 cm, it was separated from callus at the lowest end of the shoot, and subcultured in a rooting medium (RIM medium, equivalent to ½×MS medium, 3 g/L of Gelrite, 50 mg/L of kanamycin, 375 mg/L of Augmentin, 0.1% MES, pH 5.7). Individual plants that rooted within two weeks in the rooting medium, of which roots were cut off, were subcultured in the rooting medium compacted in a plant box for secondary selection for rooting. Individual plants that rooted in the plant box were used for the following conditioning step.

Individual plants that did not root within two weeks on the first rooting medium (plate), of which cut end was thinly cut off, was subcultured on the fresh rooting medium to induce rooting again. Individual plants for which rooting was observed on the rooting medium in the plant box was planted in soil in order to make them bear fruits and obtain seeds. These individual plants were conditioned by slowly decreasing humidity to avoid withering due to change of humidity environment and the like. Specifically, moistened soil was put into the plant box, and the rooting individual plants were planted into the box. They were placed in a high humidity condition first, and then the humidity was lowered by gradually loosening the lid. The plants sufficiently conditioned in the plant box over about one month were planted in bowls, and allowed to grow.

For the plants obtained after the second selection for rooting, confirmation was carried out by PCR to know whether the target gene was introduced. One true leaf of about 5 mm was cut off, and the genomic DNA was extracted by the CTAB method. Gene transfer was checked by the PCR method using 1 µL of a solution of the genomic DNA finally suspended in 300 µL of TE. As the primers, a primer set providing amplification of the kanamycin resistance gene (NPT2 gene) and a primer set providing amplification of a region containing an artificially transcribed gene and the NOS terminator were designed and used.

(e) Extraction of Proteins from Transformants

Each leaf of 1 to 2 cm of transformed plant was collected in a microtube. The leaves were frozen by adding liquid nitrogen, and finely crushed by using a homogenization pestle. After the liquid nitrogen evaporated, the residue was added with 200 μL of an SDS sample buffer (0.125 M Tris-HCl (pH 6.8), 4% SDS, 20% glycerol, 0.01% BPB, 10% 2-ME), and further mashed. The resultant was kept at 95° C. for 10 minutes, and then centrifuged, and the supernatant was transferred to a new microtube. This sample was used as proteins extracted from the plant.

(f) Western Blotting

The extracted protein (1 μL) was electrophoresed in 12% SDS polyacrylamide gel. As a molecular weight marker, Perfect Protein Western Marker (Novagen) was simultaneously electrophoresed. The proteins were blotted from the acrylamide gel to a PVDF membrane, and then the proteins were confirmed by using Ponceau S. The membrane was shaken with a blocking solution (5% skim milk, 0.05% Tween 20, PBS), and then reacted with peroxidase-labeled anti-HA antibody. As the antibody for the molecular weight marker, S-protein HRP was also simultaneously reacted. An X-ray film was exposed by using an ECL chemiluminescence system, and signals were detected. On the basis of sizes and intensities of the signals, it was verified whether AZP was expressed within the transformed plant.

(2) Virus Infection Experiment (a) Preparation of Plasmid for Virus Infection.

Figure 20:
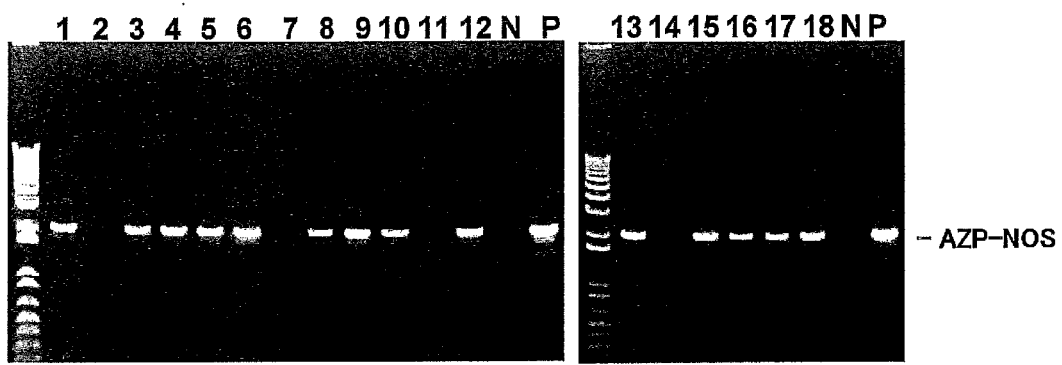
FIG. 20 This figure depicts the results of determination of copy number of the inserted AZP gene in the transformant T2 obtained by introducing AZP-2, which determination was performed by PCR. The results of PCR performed by using DNAs extracted from T2 plants derived from a specific transformant T1 (Lanes 1 to 18), DNA extracted from a wild-type tomato (N), and the binary vector used for the transformation (P) are shown.

Virus infection was attained by using the infectivity of an *agrobacterium*. In order to introduce a virus genome copy having two replication origins into a binary plasmid, objective plasmids were prepared by the two steps described below for two kinds of viruses, TYLCV and TYLCV-mild. TYLCV-mild is different from TYLCV in the direct repeats sequence to which Rep binds, and this virus was used to examine general usability for geminiviruses.

A DNA fragment corresponding to 0.5 copy containing the replication origin was amplified by PCR from the virus genomic DNA of TYLCV, and cloned into the binary plasmid pBI121 at the EcoRI/HindIII sites to obtain pBI-TYLCV(0.5). Correctness of the nucleotide sequence was confirmed by sequencing. When a PCR-amplified DNA is cloned to introduce a DNA fragment corresponding to one copy of TYLCV, it is necessary to confirm the nucleotide sequence of the prepared plasmid. However, the objective plasmid contains 1.5 copies of the virus genome, and therefore necessarily has an overlapping DNA region, and thus correctness of the nucleotide sequence cannot be confirmed by sequencing. Therefore, it was decided to once incorporate 1 copy of the virus genome into the cloning plasmid pBluescript II KS+, and then confirm the whole nucleotide sequence and further introduce a DNA fragment excised with restriction enzyme into pBI-TYLCV(0.5) without performing PCR.

A DNA fragment corresponding to 1 copy containing the replication origin was amplified by PCR from the virus genomic DNA of TYLCV, and cloned into pBluescript II KS+ at the PstI/HindIII sites to obtain pBS-TYLCV. Correctness of the nucleotide sequence was confirmed by sequencing. Then, a DNA fragment corresponding to 1 copy of the virus genome was excised from pBS-TYLCV with BsrGI and HindIII, purified on agarose gel, and then cloned into pBI-TYLCV(0.5) at the BsrGI/HindIII sites to finally obtain the objective plasmid pBI-TYLCV(1.5). The same procedure was performed for TYLCV-mild to finally obtain the objective plasmid pBI-TYLCV-mild(1.5).

(b) Confirmation of Infection Ability of Plasmid for Virus Infection

Competent cells of the *agrobacterium* C58C1RifR (GV2260) were prepared. These competent cells were introduced with the prepared binary vector containing 1.5 copy of the TYLCV genome or the TYLCV-mild genome, and a glycerol stock of the *agrobacterium* for agroinoculation was prepared, and stored at −80° C. One day before infecting a wild-type tomato, the above glycerol stock was inoculated into 6 mL of the LB medium (containing 100 mg/L of kanamycin and 50 mg/L of ampicillin), and culture was performed at 30° C. for one whole day and night. Then, the *agrobacterium* cells were collected, and suspended in 1 mL of a buffer. This suspension was injected into a cotyledon of seedling about 10 days after the seeding to infect the plant. After the infection, the plant individuals were observed at regular intervals, and viral DNA in the leaves was regularly detected. DNA samples for this purpose were prepared as described above, and on the basis of analysis of PCR product obtained by using a primer set specific to each TYLCV, virus infection was evaluated at the molecular level.

(3) Evaluation of Resistance to TYLCV Infection

The suspension of the *agrobacterium* harboring the virus binary vector was injected into a seedling obtained from a transformant T3, and symptoms of the infection were macroscopically observed over time. Further, DNA was extracted from leaves of the infected tomato, and whether the virus proliferated in the plant body was verified by PCR according to the method described in the previous section.

2. Results (1) Preparation of AZP-Transformed Tomato

Each AZP gene was introduced into the Micro-Tom tomatoes using the *agrobacterium*. Agrobacteria transformed with the binary vector having each of the AZP expression cassettes shown in FIG. 15 were used to infect cotyledon sections and thereby introduce the gene. Then, callus formation was induced by using a medium containing kanamycin, and shooting and then rooting were induced. At the time of induction of rooting, individual plants showing deep rooting into the agar medium were selected to further select the transformants, and they were conditioned and planted into soil to obtain transformants.

It was confirmed that these transformants T1 had the AZP gene by PCR. In order to detect the kanamycin resistance gene and the AZP gene, PCR was performed by using the PCR primer set shown in FIG. 16 (they were indicated with the orange and blue arrows, respectively, in the figure). Both the genes were detected in the resulting transformants as shown in FIG. 17, and thus it was confirmed that the transformation operation was successfully performed. For further confirmation, it was further determined that the whole region of the AZP expression cassette was inserted into the tomato genome by using another primer set (FIG. 18, indicated with pink arrows). It was confirmed that the whole region of the AZP expression cassette from the 35S promoter to the NOS terminator was introduced into the plant genome as shown in FIG. 19.

(2) Preparation of T2 and T3 Plants and Analysis of Each Line

The copy number of the AZP gene in the resulting T1 plant was determined by determining ratio of individuals of T2 plants in which the AZP gene was inserted, and performing the chi square test. Specifically, in T2 individuals obtained by collecting T2 seeds from each T1 line, and seeding them, presence or absence of the AZP gene was determined by PCR. The results for the T2 plants obtained by introducing AZP-2 are shown in FIG. 19 for one line of each as examples. As shown in the results shown in FIG. 19, for example, it was confirmed by PCR that, among the 18 individuals of the T2 plants obtained from a specific T1 line, 13 individual plants had the AZP gene, and thus the segregation ratio was 13:5. If this T1 line had 1 copy of the AZP gene, the segregation ratio should become 3:1. Therefore, if it is assumed that 1 copy was inserted for the chi-square test, the square value of chi is 0.074, the critical value for P=0.01 is 6.63, and therefore this null hypothesis is not rejected. On the other hand, if it is assumed that 2 copies were inserted, the square value of chi is 14.2, which is larger than the critical value, and therefore this null hypothesis is rejected. On the basis of the results of the above verification, it can be seen that 1 copy was inserted in this T1 line. Selection of 1 copy-inserted individuals was also performed for the other T1 individual plants (FIG. 20).

Further, expression of AZP in the transformants obtained by each approach was confirmed by Western blotting. An HA epitope tag was attached to the AZP expression cassette used for each approach beforehand, so that expression of the AZP protein in each transformant was successfully verified by Western blotting using an anti-HA antibody. As shown in FIG. 21, it was confirmed that the AZP protein was strongly expressed also in the T2 plants introduced with AFP-2.

Whether each T2 line obtained from a T1 plant, for which insertion of 1 copy of the AZP gene was confirmed, was homozygote or heterozygote was determined by PCR analysis of T3 seedlings obtained from each T2 plant. In PCR analysis of DNA samples extracted from leaves of T3 seedlings obtained from each T2 line (seedlings of about 20 individuals were used for each line), if retention of the AZP gene is confirmed for all the seedlings, it can be concluded that the parent plant thereof, T2 line, is homozygote (if the segregation ratio is 1:3, the parent plant thereof, T2 line, is heterozygote). Since all the T3 plants obtained from the same T2 line contained the AZP gene, it was found that this T2 line was homozygote (FIG. 22). It was also confirmed by statistical operation that the plant was a homozygote. Further, it was also confirmed by Western blotting that AZP was expressed also in the T3 plants (FIG. 23). The same operations were performed for the plants transformed with AFP-3 by using T3 seedlings obtained from each T2 plant, and similar results were obtained.

TABLE 1

|  | AZP-2 |
| --- | --- |
| Normal type T1 plant | 19 |
| One copy-inserted T1 | 12 |
| Multiple copy-inserted T1 | 2 |
| (Copy number-unidentified T1) | (5) |
| T1 providing homozygous T2 | 6 |
| T1 not providing homozygous T2 | 1 |
| (T1 not identified to be homozygous) | (5) |

Note:
The result for "T1 providing homozygous T2" line is a result obtained by analyzing the resulting 1 copy-inserted T1.

(3) Preparation of TYLCV Binary Plasmid and Confirmation of Infection Ability Thereof.

Figure 24:
FIG. 24 This figure depicts the results of infection by TYLCV established in a wild-type Micro-Tom tomato by injecting an *agrobacterium* bacterium having the TYLCV genome into the tomato plant by the agroinoculation method. In the grown individual (right), the characteristic symptoms of TYLCV infection, curling and yellowing of leaves, were distinctly observed, and evident inhibition of growth was observed.

It was studied whether or not it was possible to infect a Micro-Tom tomato by the agroinoculation method. It was attempted to infect a plurality of wild-type Micro-Tom plants with TYLCV by injecting an *agrobacterium* containing the TYLCV genome into the plants. The test was performed a plurality of times, and the infection was successfully attained at high efficiency each time. On the day 10 after the infection, shrinkage of young leaves characteristic to the TYLCV infection was observed. In the further grown individuals, curling and yellowing of the leaves, the characteristic symptoms of the TYLCV infection, were clearly observed. Evident growth inhibition was observed in the infected individual plants (FIG. 24), and although bloom was observed for many plant individuals, the probability of fruiting was extremely low.

Infection of TYLCV attained by the agroinoculation method was also confirmed at the molecular level. After the establishment of infection, leaves were collected at each stage, and the TYLCV genomic DNA was successfully detected in all the infected leaves by PCR. Further, when the same experiment was also performed for TYLCV-mild, symptoms of infection were mild, unlike TYLCV. In particular, the symptom in early stages of the infection was only color fading in peripheries of leaves, and it might be difficult to determine the infection on the basis of phenotypes. Therefore, in addition to the determination on the basis of phenotypes, identification of the replication of TYLCV-mild in the infected individuals at the molecular level by PCR enables more accurate determination.

(4) Acquisition of Resistance to TYLCV Infection Provided by Expression of AZP

Figure 25:
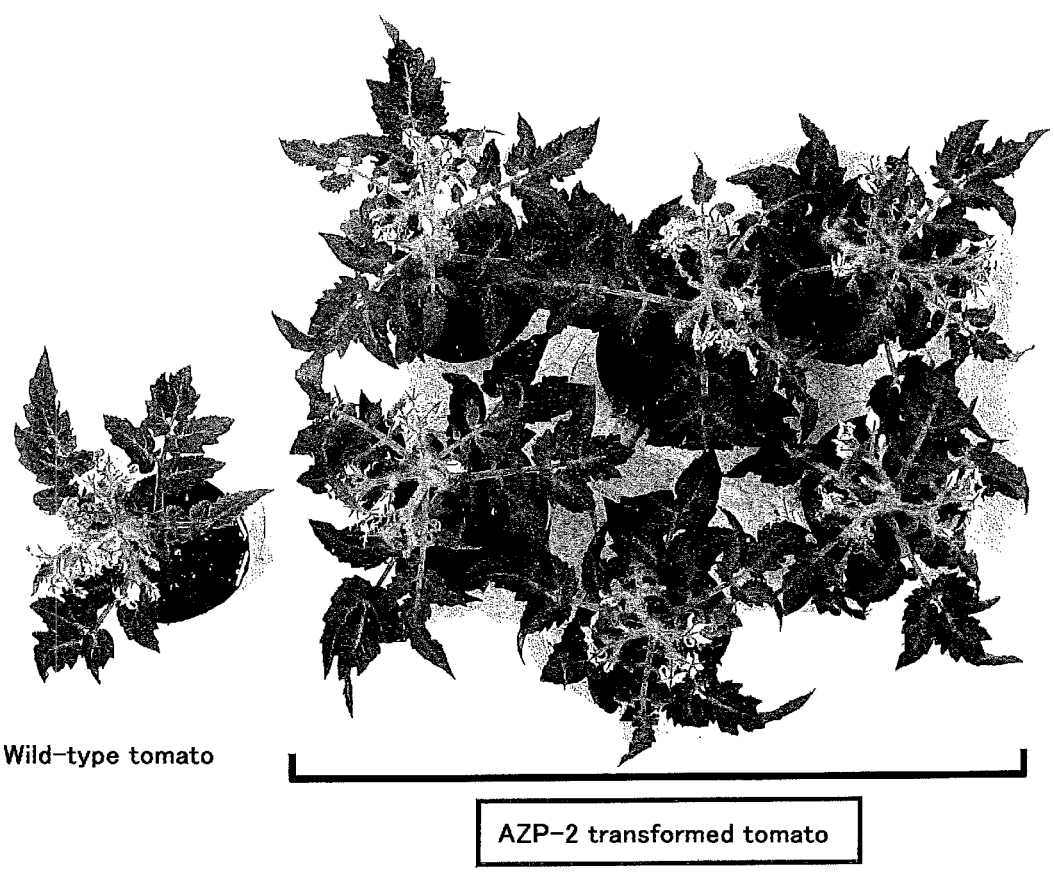
FIG. 25 This figure depicts the result of TYLCV infection test of T3 plant obtained by introducing AZP-2. Any symptom of the infection was not observed in the transformant FIG. 26 This figure depicts the results of PCR performed for leaves collected from the AZP-2-transformed tomatoes 30 days after the virus infection by using primers for TYLCV detection.
Figure 26:
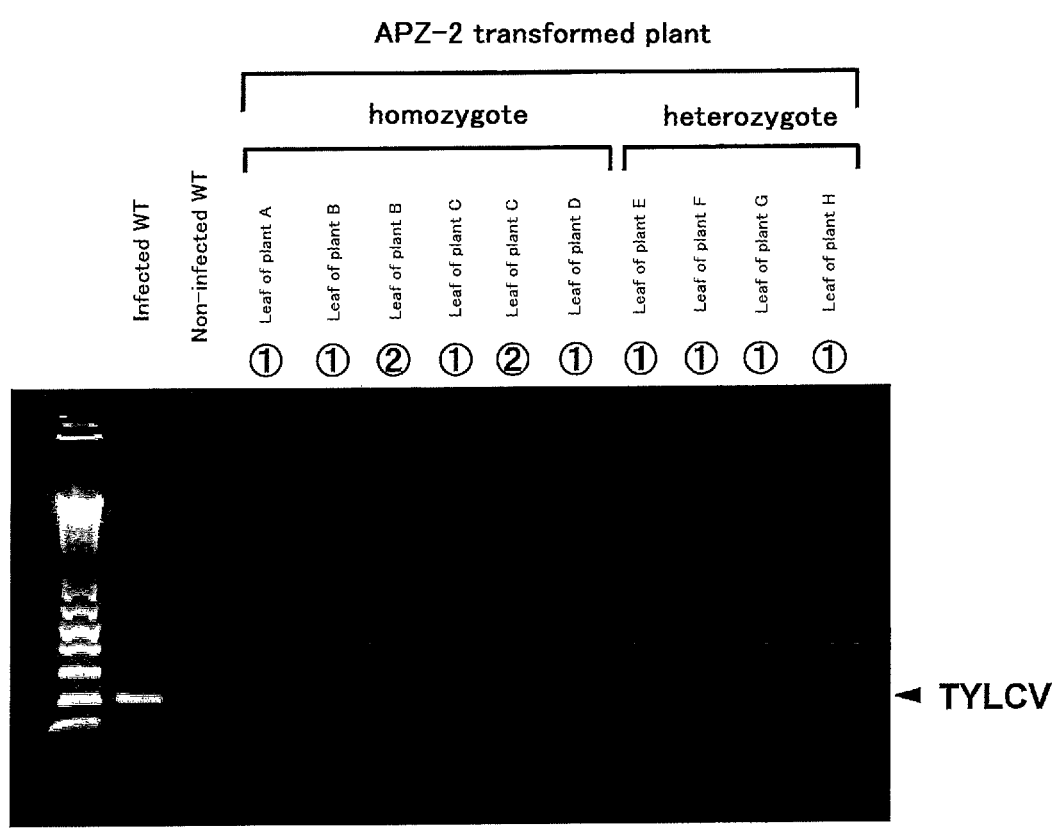

T3 plants obtained from homozygous T2 lines each obtained from 3 individuals among the T1 plants prepared by introducing AZP-2 (refer to Table 1) were infected with TYLCV in the same manner as described above. As shown in FIG. 25, shrinkage and yellowing of leaves observed in the infected wild-type plants (shown on the left of the figure) were not observed in the transformed tomatoes. The resistance to the infection was further evaluated at the molecular level by PCR. As shown in FIG. 26, any viral DNA was not detected in a T3 homozygote. Further, viral DNA was not detected not only in the homozygotes, but also in the heterozygotes, and thus proliferation of the virus was not observed.

Figure 27:
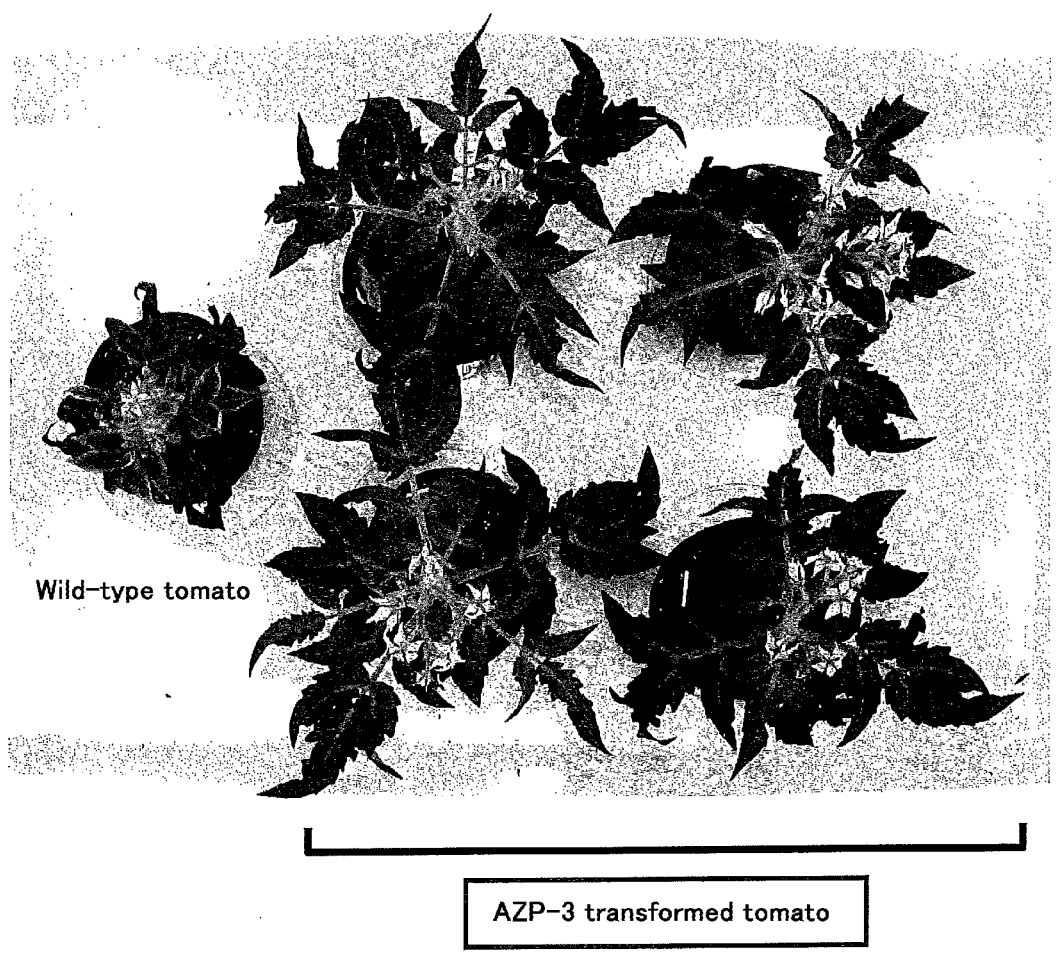
FIG. 27 This figure depicts the results of TYLCV infection in T3 plants obtained from one T1 plant individual prepared by introducing AZP-3.
Figure 28:
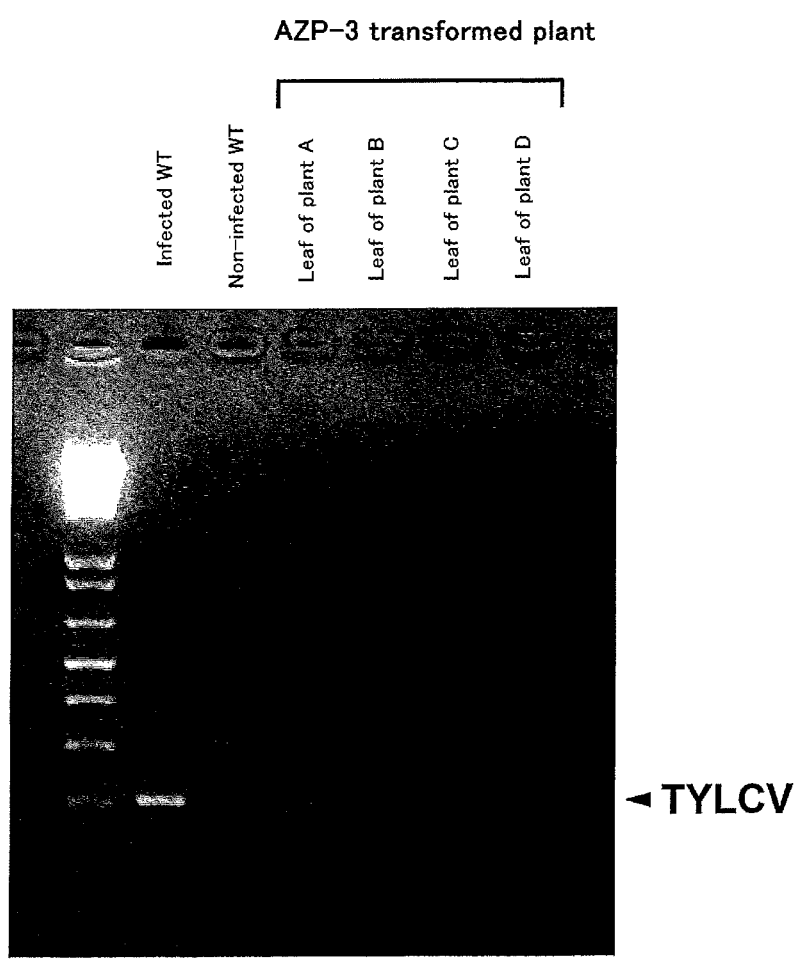
FIG. 28 This figure depicts that viral DNA was not detected in AZP-3 transformants.

Further, when T3 plants obtained from one individual of the T1 plant prepared by introducing AZP-3 were infected with TYLCV in the same manner as described above, shrinkage and yellowing of leaves observed in the infected wild-type plants were not observed in the transformed tomatoes, as shown in FIG. 27. Furthermore, viral DNA was not detected in the transformant obtained with AZP-3, either, as shown in FIG. 28.

INDUSTRIAL APPLICABILITY

The replication inhibitor of the present invention can exhibit high efficacy against TYLCV and other geminiviruses. Therefore, the inhibitor is very useful as a means for controlling various geminiviruses.

What is claimed is:

1. A geminivirus replication inhibitor, which comprises a zinc finger protein that can specifically bind to full length DNA of stem loop region of a geminivirus, or one or more partial DNAs selected from the full length DNA, and can inhibit formation of a stem loop structure by specific binding of said zinc finger protein to said DNA, and can inhibit formation of a stem loop structure and thus can inhibit cleavage of a single strand DNA of a loop structure in the stem loop structure by replication protein (Rep) of the geminivirus, wherein said zinc finger protein is any of the following proteins:

(a) a protein having the amino acid sequence shown as SEQ ID NO: 1 or 2; or (b) a protein having a homology of 90% or more to the amino acid sequence specified as SEQ ID NO: 1 or 2, and having substantially the same replication inhibitory action as that of a protein comprising the amino acid sequence specified as SEQ ID NO: 1 or 2.

2. The replication inhibitor according to claim 1, which contains a single zinc finger protein that can bind to one partial DNA selected from the full length DNA of the stem region of the geminivirus, or a single zinc finger protein that can bind to two or more partial DNAs selected from the full length DNA.

3. The replication inhibitor according to claim 1, which contains a zinc finger protein formed by binding two or more zinc finger proteins, with a linker or linkers, that can bind to respective two or more partial DNAs selected from the full length DNA of the stem region of the geminivirus.

4. The replication inhibitor according to claim 3, wherein two of the zinc finger proteins consist of a zinc finger protein comprising three zinc finger domains and a zinc finger protein comprising six zinc finger domains.

5. The replication inhibitor according to claim 3, wherein the linker is a peptide linker.

6. The replication inhibitor according to claim 1, wherein the geminivirus is a virus belonging to the genus *Begomovirus*.

7. The replication inhibitor according to claim 6, wherein the geminivirus is a tomato yellow leaf curl virus.

8. A nucleic acid encoding the zinc finger protein mentioned in claim 1.

9. A recombinant vector for transformation of a plant, which contains the nucleic acid according to claim 8.

10. An agricultural chemical comprising the zinc finger protein according to claim 1 or a nucleic acid encoding the zinc finger protein as an active ingredient.

11. A gene recombinant plant that is transformed with the nucleic acid of claim 8, which is a plant having resistance against a geminivirus, and can express the zinc finger protein.

12. A plant transformed by introducing the nucleic acid encoding the zinc finger protein according to claim 8.

13. A method for allowing a plant to acquire resistance against a geminivirus, which comprises the step of transforming the plant by introducing the nucleic acid encoding the zinc finger protein according to claim 8 into the plant.

14. A vector for transformation of a plant, which contains a nucleic acid encoding the zinc finger protein mentioned in claim 1.

15. The replication inhibitor according to claim 4, wherein the linker is a peptide linker.

16. The replication inhibitor according to claim 2, wherein the geminivirus is a virus belonging to the genus *Begomovirus*.

17. The replication inhibitor according to claim 3, wherein the geminivirus is a virus belonging to the genus *Begomovirus*.

18. The replication inhibitor according to claim 4, wherein the geminivirus is a virus belonging to the genus *Begomovirus*.

19. The replication inhibitor according to claim 5, wherein the geminivirus is a virus belonging to the genus *Begomovirus*.

\* \* \* \* \*

SEQUENCE LISTING

<160> NUMBER OF SEQ ID NOS: 21

<210> SEQ ID NO 1
<211> LENGTH: 283
<212> TYPE: PRT
<213> ORGANISM: Artificial Sequence
<220> FEATURE:
<223> OTHER INFORMATION: Synthetic Construct

<400> SEQUENCE: 1

```
Gly Glu Lys Pro Tyr Lys Cys Pro Glu Cys Gly Lys Ser Phe Ser Arg
1               5                   10                  15

Ser Ser Asp Leu Gln Glu His Gln Arg Thr His Thr Gly Glu Lys Pro
                20                  25                  30

Tyr Lys Cys Pro Glu Cys Gly Lys Ser Phe Ser Arg Ser Ser His Leu
            35                  40                  45

Gln Thr His Gln Arg Thr His Thr Gly Glu Lys Pro Tyr Lys Cys Pro
        50                  55                  60

Glu Cys Gly Lys Ser Phe Ser Gln Ser Asn His Leu Gln Arg His Gln
65                  70                  75                  80

Arg Thr His Thr Gly Glu Lys Pro Tyr Lys Cys Pro Glu Cys Gly Lys
                85                  90                  95

Ser Phe Ser Glu Ser Asp Asp Leu Gln Gln His Gln Arg Thr His Thr
                100                 105                 110

Gly Glu Lys Pro Tyr Lys Cys Pro Glu Cys Gly Lys Ser Phe Ser Thr
            115                 120                 125

Ser Thr Ser Leu Gln Gln His Gln Arg Thr His Thr Gly Glu Lys Pro
        130                 135                 140

Tyr Lys Cys Pro Glu Cys Gly Lys Ser Phe Ser Thr Ser Thr Asn Leu
145                 150                 155                 160

Gln Gln His Gln Arg Thr His Thr Gly Glu Lys Pro Tyr Lys Cys Pro
                165                 170                 175

Glu Cys Gly Lys Ser Phe Ser Thr Ser Thr Asn Leu Gln Thr His Gln
                180                 185                 190

Arg Thr His Thr Gly Glu Lys Pro Tyr Lys Cys Pro Glu Cys Gly Lys
            195                 200                 205

Ser Phe Ser Arg Ser Asn Asp Leu Gln Glu His Gln Arg Thr His Thr
        210                 215                 220

Gly Glu Lys Pro Tyr Lys Cys Pro Glu Cys Gly Lys Ser Phe Ser Thr
225                 230                 235                 240

Ser Ser Asn Leu Gln Glu His Gln Arg Thr His Thr Gly Glu Lys Pro
                245                 250                 255

Tyr Lys Cys Pro Glu Cys Gly Lys Ser Phe Ser Glu Ser Ser His Leu
                260                 265                 270

Gln Arg His Gln Arg Thr His Thr Gly Glu Lys
            275                 280
```

<210> SEQ ID NO 2
<211> LENGTH: 264
<212> TYPE: PRT
<213> ORGANISM: Artificial Sequence
<220> FEATURE:
<223> OTHER INFORMATION: Synthetic Construct

<400> SEQUENCE: 2

```
Gly Glu Lys Pro Tyr Lys Cys Pro Glu Cys Gly Lys Ser Phe Ser Arg
1               5                   10                  15

Ser Ser Asp Leu Gln Glu His Gln Arg Thr His Thr Gly Glu Lys Pro
                20                  25                  30

Tyr Lys Cys Pro Glu Cys Gly Lys Ser Phe Ser Arg Ser Ser His Leu
            35                  40                  45

Gln Thr His Gln Arg Thr His Thr Gly Glu Lys Pro Tyr Lys Cys Pro
```

```
              50                  55                  60
Glu Cys Gly Lys Ser Phe Ser Gln Ser Asn His Leu Gln Arg His Gln
 65                  70                  75                  80

Arg Thr His Thr Gly Glu Lys Pro Tyr Lys Cys Pro Glu Cys Gly Lys
                 85                  90                  95

Ser Phe Ser Glu Ser Asp Asp Leu Gln Gln His Gln Arg Thr His Thr
                100                 105                 110

Gly Glu Lys Pro Tyr Lys Cys Pro Glu Cys Gly Lys Ser Phe Ser Thr
                115                 120                 125

Ser Thr Ser Leu Gln Gln His Gln Arg Thr His Thr Gly Glu Lys Pro
            130                 135                 140

Tyr Lys Cys Pro Glu Cys Gly Lys Ser Phe Ser Thr Ser Thr Asn Leu
145                 150                 155                 160

Gln Gln His Gln Arg Thr His Thr Gly Glu Lys Arg Thr Gly Thr Gly
                165                 170                 175

Ser Gly Glu Lys Pro Tyr Lys Cys Pro Glu Cys Gly Lys Ser Phe Ser
                180                 185                 190

Arg Ser Asn Asp Leu Gln Glu His Gln Arg Thr His Thr Gly Glu Lys
                195                 200                 205

Pro Tyr Lys Cys Pro Glu Cys Gly Lys Ser Phe Ser Thr Ser Ser Asn
210                 215                 220

Leu Gln Glu His Gln Arg Thr His Thr Gly Lys Pro Tyr Lys Cys
225                 230                 235                 240

Pro Glu Cys Gly Lys Ser Phe Ser Glu Ser His Leu Gln Arg His
                245                 250                 255

Gln Arg Thr His Thr Gly Glu Lys
                260

<210> SEQ ID NO 3
<211> LENGTH: 849
<212> TYPE: DNA
<213> ORGANISM: Artificial Sequence
<220> FEATURE:
<223> OTHER INFORMATION: Synthetic Construct

<400> SEQUENCE: 3
ggggagaagc cgtataaatg tccggaatgt ggtaaaagtt ttagccgtag ctctgatttg      60
caggaacatc agcgtaccca taccggtgaa aaaccataca aatgtccaga gtgcggcaaa     120
tctttctctc gttcttctca tcttcagact catcagcgta ctcacactgg cgagaagcct     180
tacaagtgcc ctgaatgcgg gaagagcttt agtcaaagta atcatttaca acgtcaccaa     240
cgcacgcaca cggggagaa gccgtataaa tgtccggaat gtggtaaaag ttttagcgaa     300
agcgatgatt tgcagcaaca tcagcgtacc ataccggtg aaaaaccata caaatgtcca     360
gagtgcggca atctttctc tacttctact tctcttcagc aacatcagcg tactcacact     420
ggcgagaagc ttacaagtg ccctgaatgc gggaagagct ttagtactag tactaattta     480
caacaacacc aacgcacgca cacggggga agccgtata atgtccgga atgtggtaaa     540
agttttagca cttctactaa tcttcagact caccaacgca cgcacacggg ggagaagccg     600
tataaatgtc cggaatgtgg taaaagtttt agccgtagca atgatttgca ggaacatcag     660
cgtacccata ccggtgaaaa accatacaaa tgtccagagt gcggcaaatc tttctctact     720
tcttctaatc ttcaggaaca tcagcgtact cacactggcg agaagcctta caagtgccct     780
gaatgcggga agagctttag tgaaagttct catttacaac gtcaccaacg cacgcacacg     840
```

```
ggggagaag                                                                      849

<210> SEQ ID NO 4
<211> LENGTH: 792
<212> TYPE: DNA
<213> ORGANISM: Artificial Sequence
<220> FEATURE:
<223> OTHER INFORMATION: Synthetic Construct

<400> SEQUENCE: 4
ggggagaagc cgtataaatg tccggaatgt ggtaaaagtt ttagccgtag ctctgatttg      60
caggaacatc agcgtaccca taccggtgaa aaaccataca aatgtccaga gtgcggcaaa     120
tctttctctc gttcttctca tcttcagact catcagcgta ctcacactgg cgagaagcct     180
tacaagtgcc ctgaatgcgg gaagagcttt agtcaaagta atcatttaca acgtcaccaa     240
cgcacgcaca cggggagaa gccgtataaa tgtccggaat gtggtaaaag ttttagcgaa      300
agcgatgatt tgcagcaaca tcagcgtacc cataccggtg aaaaaccata caaatgtcca     360
gagtgcggca atctttctc tacttctact tctcttcagc aacatcagcg tactcacact     420
ggcgagaagc cttacaagtg ccctgaatgc gggaagagct tagtactag tactaattta     480
caacaacacc aacgcacgca cacggggag aagcgtacgg gtaccggatc cggggagaag     540
ccgtataaat gtccggaatg tggtaaaagt tttagccgta gcaatgattt gcaggaacat     600
cagcgtaccc ataccggtga aaaaccatac aaatgtccag agtgcggcaa atctttctct     660
acttcttcta atcttcagga acatcagcgt actcacactg gcgagaagcc ttacaagtgc     720
cctgaatgcg ggaagagctt tagtgaaagt tctcatttac aacgtcacca acgcacgcac     780
acggggagaa ag                                                          792

<210> SEQ ID NO 5
<211> LENGTH: 33
<212> TYPE: DNA
<213> ORGANISM: Tomato yellow leaf curl virus

<400> SEQUENCE: 5
gcggccatcc gtataatatt accggatggc cgc                                    33

<210> SEQ ID NO 6
<211> LENGTH: 33
<212> TYPE: DNA
<213> ORGANISM: Bean dwarf mosaic virus

<400> SEQUENCE: 6
gcggccatcc gtataatatt accggatggc cgc                                    33

<210> SEQ ID NO 7
<211> LENGTH: 33
<212> TYPE: DNA
<213> ORGANISM: Tomato golden mosaic virus

<400> SEQUENCE: 7
gcggccatcc gtttaatatt accggatggc cgc                                    33

<210> SEQ ID NO 8
<211> LENGTH: 34
<212> TYPE: DNA
<213> ORGANISM: Abutilon mosaic virus

<400> SEQUENCE: 8
gcggccatcc gctataatat taccggatgg ccgc                                   34
```

<210> SEQ ID NO 9
<211> LENGTH: 34
<212> TYPE: DNA
<213> ORGANISM: Bean golden mosaic virus

<400> SEQUENCE: 9
gcggccatcc gctataatat taccggatgg ccgc                    34

<210> SEQ ID NO 10
<211> LENGTH: 34
<212> TYPE: DNA
<213> ORGANISM: Potato yellow mosaic virus

<400> SEQUENCE: 10
gcggccatcc gttataatat taccggatgg ccgc                    34

<210> SEQ ID NO 11
<211> LENGTH: 34
<212> TYPE: DNA
<213> ORGANISM: Tomato mottle virus

<400> SEQUENCE: 11
gcggccatcc gcaataatat taccggatgg ccgc                    34

<210> SEQ ID NO 12
<211> LENGTH: 33
<212> TYPE: DNA
<213> ORGANISM: Artificial Sequence
<220> FEATURE:
<223> OTHER INFORMATION: Synthetic replication inhibitor

<400> SEQUENCE: 12
gcggccatcc gtataatatt accggatggc cgc                     33

<210> SEQ ID NO 13
<211> LENGTH: 33
<212> TYPE: DNA
<213> ORGANISM: Tomato yellow leaf curl virus
<220> FEATURE:
<221> NAME/KEY: misc_feature
<223> OTHER INFORMATION: stem loop region of TYLCV

<400> SEQUENCE: 13
gcggccatcc gtataatatt accggatggc cgc                     33

<210> SEQ ID NO 14
<211> LENGTH: 33
<212> TYPE: DNA
<213> ORGANISM: Bean dwarf mosaic virus

<400> SEQUENCE: 14
gcggccatcc gtataatatt accggatggc cgc                     33

<210> SEQ ID NO 15
<211> LENGTH: 33
<212> TYPE: DNA
<213> ORGANISM: Tomato golden mosaic virus

<400> SEQUENCE: 15
gcggccatcc gtttaatatt accggatggc cgc                     33

<210> SEQ ID NO 16
<211> LENGTH: 34

```
<212> TYPE: DNA
<213> ORGANISM: Abutilon mosaic virus

<400> SEQUENCE: 16
gcggccatcc gctataatat taccggatgg ccgc                                34

<210> SEQ ID NO 17
<211> LENGTH: 34
<212> TYPE: DNA
<213> ORGANISM: Bean golden mosaic virus

<400> SEQUENCE: 17
gcggccatcc gctataatat taccggatgg ccgc                                34

<210> SEQ ID NO 18
<211> LENGTH: 34
<212> TYPE: DNA
<213> ORGANISM: Potato yellow mosaic virus

<400> SEQUENCE: 18
gcggccatcc gttataatat taccggatgg ccgc                                34

<210> SEQ ID NO 19
<211> LENGTH: 34
<212> TYPE: DNA
<213> ORGANISM: Tomato mottle virus

<400> SEQUENCE: 19
gcggccatcc gcaataatat taccggatgg ccgc                                34

<210> SEQ ID NO 20
<211> LENGTH: 33
<212> TYPE: DNA
<213> ORGANISM: Unknown
<220> FEATURE:
<223> OTHER INFORMATION: Stem loop region of various geminiviruses,
      including viruses belong to the genus Begomovirus

<400> SEQUENCE: 20
gcggccatcc gtataatatt accggatggc cgc                                 33

<210> SEQ ID NO 21
<211> LENGTH: 31
<212> TYPE: DNA
<213> ORGANISM: Artificial Sequence
<220> FEATURE:
<223> OTHER INFORMATION: Synthetic

<400> SEQUENCE: 21
ggccatccgt ataatattac cggatggccg c                                   31
```